(12) United States Patent
Ebbitt

(10) Patent No.: US 8,439,978 B2
(45) Date of Patent: May 14, 2013

(54) PROSTHETIC DEVICE AND METHOD FOR IMPLANTING THE PROSTHETIC DEVICE

(75) Inventor: Peter Ebbitt, Boca Raton, FL (US)

(73) Assignee: Mako Surgical Corp., Ft. Lauderdale, FL (US)

( * ) Notice: Subject to any disclaimer, the term of this patent is extended or adjusted under 35 U.S.C. 154(b) by 114 days.

(21) Appl. No.: 12/330,305

(22) Filed: Dec. 8, 2008

(65) Prior Publication Data

US 2009/0192620 A1 Jul. 30, 2009

Related U.S. Application Data

(60) Provisional application No. 61/005,990, filed on Dec. 10, 2007.

(51) Int. Cl.
A61F 2/36 (2006.01)
A61F 2/30 (2006.01)

(52) U.S. Cl.
USPC .................. 623/23.12; 623/18.11; 623/23.11

(58) Field of Classification Search .... 623/22.11–23.14, 623/18.11, 23.12; A61F 2/32
See application file for complete search history.

(56) References Cited

U.S. PATENT DOCUMENTS

| | | | |
|---|---|---|---|
| 4,005,495 A | | 2/1977 | Locke et al. |
| 5,405,389 A * | | 4/1995 | Conta et al. ................. 623/23.55 |
| 5,800,557 A * | | 9/1998 | Elhami ........................ 623/23.12 |
| 6,758,864 B2 * | | 7/2004 | Storer et al. ............... 623/22.38 |
| 6,866,685 B2 | | 3/2005 | Chan et al. |
| 2003/0055501 A1 | | 3/2003 | Fell et al. |
| 2003/0163202 A1 | | 8/2003 | Lakin |
| 2003/0187514 A1 * | | 10/2003 | McMinn ..................... 623/22.44 |
| 2005/0085915 A1 | | 4/2005 | Steinberg |
| 2005/0256585 A1 | | 11/2005 | Park et al. |
| 2006/0142657 A1 | | 6/2006 | Quaid et al. |
| 2006/0241779 A1 * | | 10/2006 | Lakin ......................... 623/22.15 |
| 2009/0149965 A1 | | 6/2009 | Quaid |
| 2009/0157192 A1 | | 6/2009 | Stuart |

FOREIGN PATENT DOCUMENTS

| | | |
|---|---|---|
| CH | 626249 A5 | 11/1981 |
| DE | 976768 C | 4/1964 |
| DE | 2524923 B1 | 11/1976 |
| DE | 2742464 A1 | 3/1979 |
| DE | 101 30 366 A1 | 11/2002 |
| DE | 202006017005 U1 | 1/2007 |
| EP | 0084094 A1 | 7/1983 |
| EP | 1611870 A1 | 1/2006 |
| FR | 2391712 A1 | 12/1978 |
| GB | 718 935 A | 11/1954 |
| WO | WO 89/11873 | 12/1989 |

OTHER PUBLICATIONS

International Search Report corresponding to PCT Application No. PCT/US2008/085880 dated Jun. 18, 2009, 2 pages.
International Preliminary Report on Patentability cited in related International Patent Application No. PCT/US2008/085880, dated Jun. 15, 2010.
Written Opinion cited in related International Patent Application No. PCT/US2008/085880, dated Jun. 18, 2009.
International Preliminary Report on Patentability cited in related International Patent Application No. PCT/US2008/085898, dated Jun. 15, 2010.
International Search Report cited in related International Patent Application No. PCT/US2008/085898, dated Jun. 18, 2009.
Written Opinion cited in related International Patent Application No. PCT/US2008/085898, dated Jun. 18, 2009.

* cited by examiner

Primary Examiner — Thomas J Sweet
Assistant Examiner — Jason-Dennis Stewart
(74) Attorney, Agent, or Firm — Foley & Lardner LLP

(57) ABSTRACT

A substantially cup-shaped prosthetic device for a joint is provided. The prosthetic device includes an outer surface configured to operatively engage at least one of a first bone of the joint and a component, an inner surface including at least a portion configured to connect to a second bone of the joint, and at least one reservoir having an opening at each of the inner surface and the outer surface and extending therebetween.

20 Claims, 16 Drawing Sheets

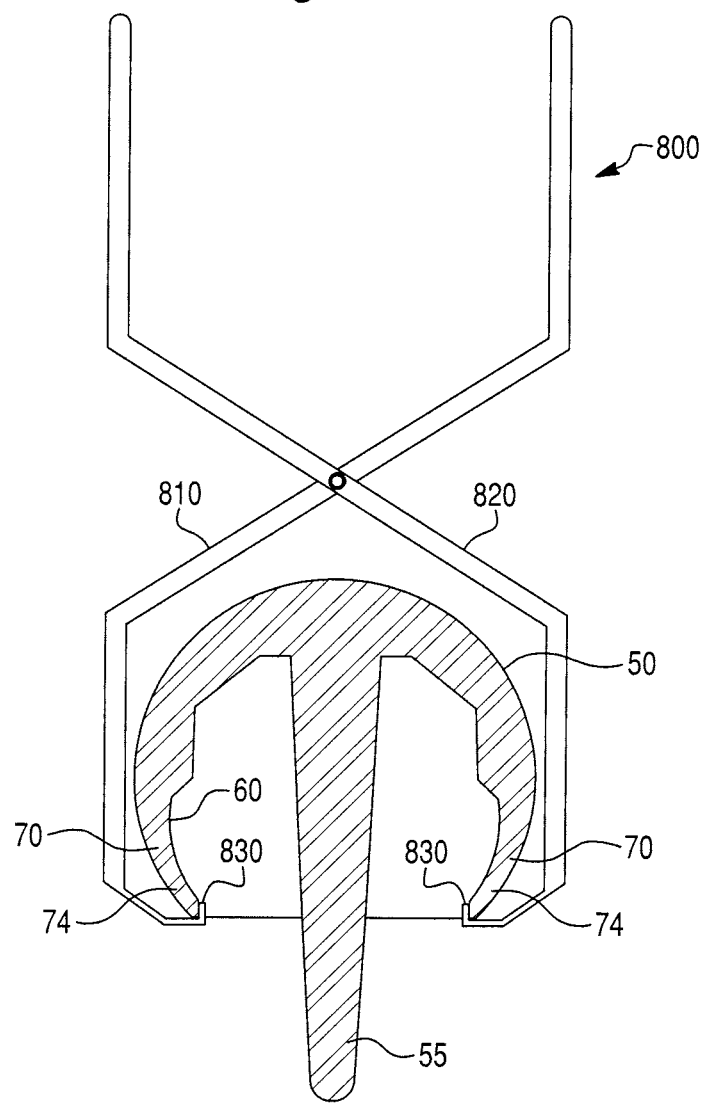

PROSTHETIC DEVICE AND METHOD FOR IMPLANTING THE PROSTHETIC DEVICE

CROSS-REFERENCE TO RELATED APPLICATIONS

The present application claims priority to U.S. Provisional Patent Application Ser. No. 61/005,990, filed Dec. 10, 2007, which is hereby incorporated by reference herein in its entirety.

BACKGROUND OF THE INVENTION

1. Field of the Invention

The invention relates to orthopedic joint replacement and, more particularly, to a prosthetic device for use in orthopedic joint replacement and a method for implanting the prosthetic device.

2. Description of Related Art

FIG. 1A illustrates the bones of a hip joint 10, including a portion of a pelvis 12 and a proximal end of a femur 14. The proximal end of the femur 14 includes a ball-shaped femoral head 16 disposed on a femoral neck 18 that is connected to a femoral shaft 20. The proximal end of the femur 14 has a superior aspect 14a and an inferior aspect 14b. As shown in FIG. 1B, the superior aspect 14a includes a vascular region 24 located near the surface of the bone and having a high concentration of retinacular vessels 24a, which supply blood to the bone tissue of the femoral head 16. As shown in FIG. 1C, the femoral head 16 fits into a concave socket in the pelvis 12 called the acetabulum 22, forming the hip joint 10. The acetabulum 22 and the femoral head 16 are covered by articular cartilage 23 and enclosed within a fibrous joint capsule 21 that is lined with a synovial membrane 25 that secretes synovial fluid 25a. The synovial fluid 25a is a viscous fluid that performs a number of functions vital to joint health, including lubricating the joint 10, delivering nutrients and oxygen to the cartilage 23, removing debris, and inhibiting bacterial growth. Additionally, the synovial fluid 25a and the cartilage 23 work together to absorb shock and reduce friction during articulation of the joint 10.

Over time, the hip joint 10 may degenerate (for example, due to osteoarthritis) resulting in pain and diminished functionality. To reduce pain and restore functionality, a hip replacement procedure (e.g., total hip arthroplasty or hip resurfacing) may be necessary. During hip replacement, a surgeon replaces portions of a patient's hip joint 10 with artificial components. In conventional total hip arthroplasty, the surgeon removes the femoral head 16 and neck 18 (shown in FIG. 2A) and replaces the natural bone with a prosthetic femoral component 26 comprising a head 26a, a neck 26b, and a stem 26c (shown in FIG. 2B). As shown in FIG. 2C, the stem 26c of the femoral component 26 is anchored in a cavity that the surgeon creates in the intramedullary canal of the femur 14. The natural acetabulum 22 of the pelvis 22 may also be replaced. For example, if the acetabulum 22 is worn or diseased, the surgeon can ream the acetabulum 22 and replace the natural surface with a prosthetic acetabular component 28 comprising a hemispherical shaped cup 28a (shown in FIG. 2B) that may include a liner 28b. In cases where the acetabulum 22 is healthy, the surgeon may leave the natural acetabulum 22 intact and replace only the femoral head 16 and neck 18.

In contrast to total hip arthroplasty, which is highly invasive, patients who have healthy subsurface bone and disease that is confined to the surface of the femoral head 16 may be candidates for hip resurfacing. In conventional hip resurfacing, the surgeon removes diseased bone from the femoral head 16 using a rotationally symmetric cutting tool, such as a cylindrical reamer 30. As shown in FIG. 3A, the surgeon centers the cylindrical reamer 30 on an axis A-A defined by a guide hole G created in the femoral head 16. In operation, the cutting element of the cylindrical reamer 30 rotates about the femoral head 16, cutting away diseased surface bone and resulting in a femoral head 16 having a rotationally symmetric surface shape 16a. As shown in FIGS. 3B and 3C, the reamed femoral head is mated with a prosthetic femoral head cup 32. The femoral head cup 32 typically has an internal surface shape that substantially corresponds to the rotationally symmetric surface shape 16a of the reamed femoral head so that the cup 32 will fit securely in place. The femoral head cup 32 also includes a central stem 32a that is received in the guide hole G to aid in alignment and stability of the femoral head cup 32. As with conventional hip arthroplasty, hip resurfacing may include replacement of the acetabulum 22 when the acetabulum 22 is damaged or diseased.

As can be seen by comparing FIGS. 2C and 3B, hip resurfacing is less invasive and preserves more bone than conventional hip arthroplasty because only a portion of the femoral head 16 is removed, leaving the femoral neck 18, the subsurface bone of the femoral head 16, and the intramedullary canal of the femur 14 intact. Although conventional hip resurfacing removes less bone than conventional hip arthroplasty, the procedure still removes a significant portion of the femoral head 16, including healthy bone. As shown in FIG. 3D, one disadvantage of the conventional resurfacing process is that the bone cuts may impinge upon the vascular region 24 of the femur 14 resulting in damage to the retinacular vessels 24a. This damage adversely impacts the blood supply to the femoral head 16, which can ultimately lead to necrosis of the bone, loosening of the implanted femoral head cup 32, pain, and femoral fracture. Additionally, if the cylindrical reamer 30 is undersized or malpositioned, there is a danger of the cylindrical reamer 30 contacting the femoral neck 18, creating a notch in the femoral neck 18. This femoral "notching" causes a stress riser in the femur 14 that increases the risk of femoral fracture, particularly if the notching occurs on the superior aspect 14a of the femoral neck 18, which is in tension during activities such as standing, walking, and running.

Another disadvantage of conventional femoral resurfacing components is that such components may lack the ability to maintain contact with a substantial portion of the articular surface of the acetabular component throughout the range of motion of the joint 10. For example, as the femur 14 moves through the range of motion, the edge of a conventional femoral head cup 32 may articulate above the rim of the acetabular cup thereby reducing the contact area between the femoral and acetabular components. Reduced contact area diminishes the load bearing capability of the component. Additionally, reduced contact area decreases the piston effect, which refers to the vacuum created between the femoral and acetabular components when a force attempts to extract the femoral component from the acetabular component. A strong piston effect creates a high vacuum, which aids in preventing joint dislocation, a painful complication in which the femoral ball disengages from the acetabular cup.

Another disadvantage of conventional hip replacement components is the potential for lever arm dislocation at the extreme range of motion due to impingement, which occurs when the femoral neck impinges on the rim of the acetabular cup creating a lever arm that forces the femoral ball out of the acetabular cup. Impingement is most likely to occur when the hip joint 10 exceeds 90 degrees of flexion, such as when the patient crosses his legs or sits in a low seat where the knees are elevated above the hips. FIGS. 4A to 4D illustrate the mechanics of lever arm dislocation using the total hip prosthesis shown in FIG. 2B. For example, at 90 degrees of flexion (FIG. 4A), the neck 26b of the femoral component 26 is near the rim of the cup-shaped acetabular component 28. If the patient continues to move (flex) the leg beyond 90 degrees (FIG. 4B), the femoral neck 26b contacts or impinges on the rim of the acetabular component 28. As shown in FIG. 4C, the femur 14 acts as a lever mechanism that pushes the femoral neck 26b against the rim of the acetabular component 28, eventually forcing the femoral head 26a out of the acetabular component 28. The resulting dislocation is illustrated in FIG. 4D.

Another disadvantage of conventional hip resurfacing components is that such components may not provide a necessary or desired amount of joint lubrication. The components rely primarily on the clearance between the femoral and acetabular components to draw fluid between the components to achieve joint lubrication. As the patient moves, the clearance angle and motion of the articular surfaces generate a hydrodynamic fluid film that lubricates the joint 10. Factors such as bone density and implant position, however, may impact the ability of the surgeon to achieve optimal clearance. As a result, the ability of the bearing to generate a lubricating fluid film may be compromised.

SUMMARY OF THE INVENTION

According to an aspect of the present invention, a substantially cup-shaped prosthetic device for a joint includes an outer surface configured to operatively engage at least one of a first bone of the joint and a component, an inner surface including at least a portion configured to connect to a second bone of the joint, and at least one reservoir having an opening at each of the inner surface and the outer surface and extending therebetween.

According to another aspect, a substantially cup-shaped prosthetic device for a joint includes an outer surface configured to operatively engage at least one of a first bone of the joint and a component, an inner surface including a portion configured to connect to a second bone of the joint, a first deflection member, and a second deflection member. The first and second deflection members each include a distal end and at least a portion that is configured to flex upon application of a force such that the distal end is displaced. Additionally, the portion of the first extension member is configured to flex at least partially independently of the portion of the second extension member.

According to yet another aspect, a method of implanting a prosthetic device in a joint includes preparing a first bone of the joint to receive a first component; expanding a base of the first component; moving the first component onto the first bone; and releasing the base of the first component to allow the base to at least partially contract.

BRIEF DESCRIPTION OF THE DRAWINGS

The accompanying drawings, which are incorporated in and constitute a part of this specification, illustrate embodiments of the invention and together with the description serve to explain principles of the invention.

FIG. 12A is an illustration of an installation tool according to the present invention.

DETAILED DESCRIPTION OF PREFERRED EMBODIMENTS

Figure 1A:
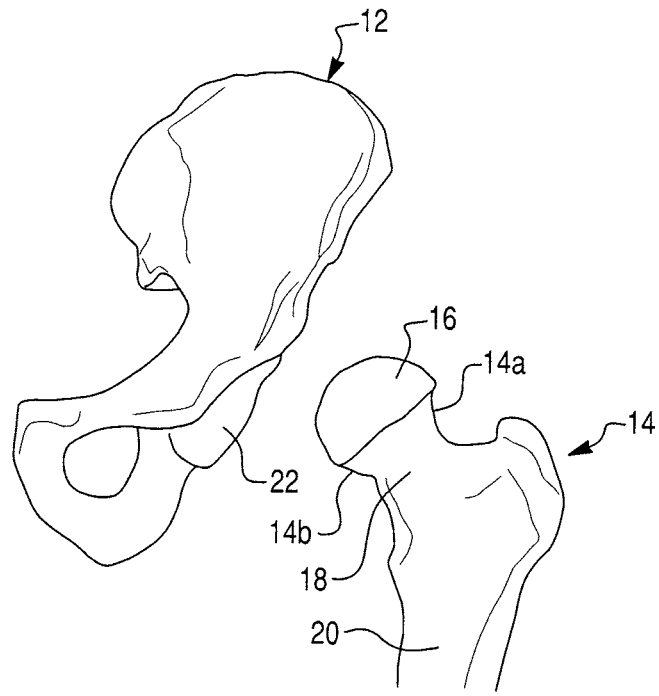
FIG. 1A is a perspective view of a femur and a pelvis.

Presently preferred embodiments of the invention are illustrated in the drawings. An effort has been made to use the same or like reference numbers throughout the drawings to refer to the same or like parts.

Figure 5A:
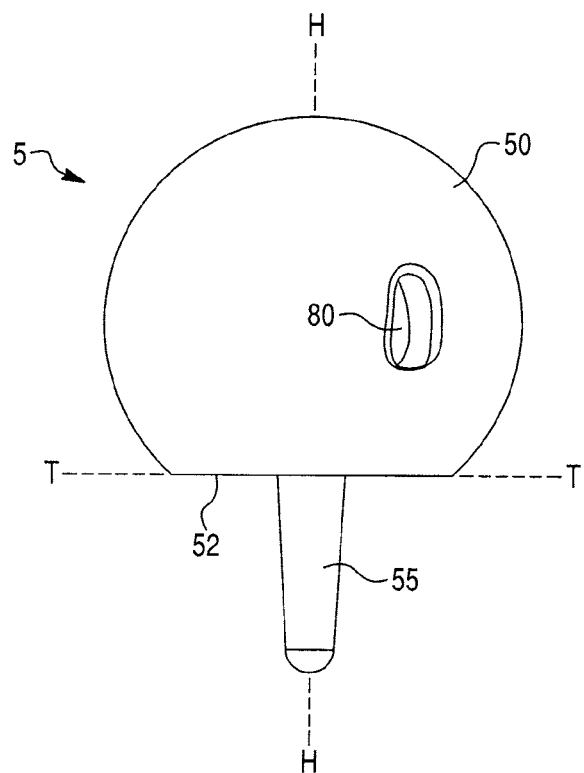
FIGS. 5A and 5B are perspective views of an embodiment of a prosthetic device according to the present invention.
Figure 5B:
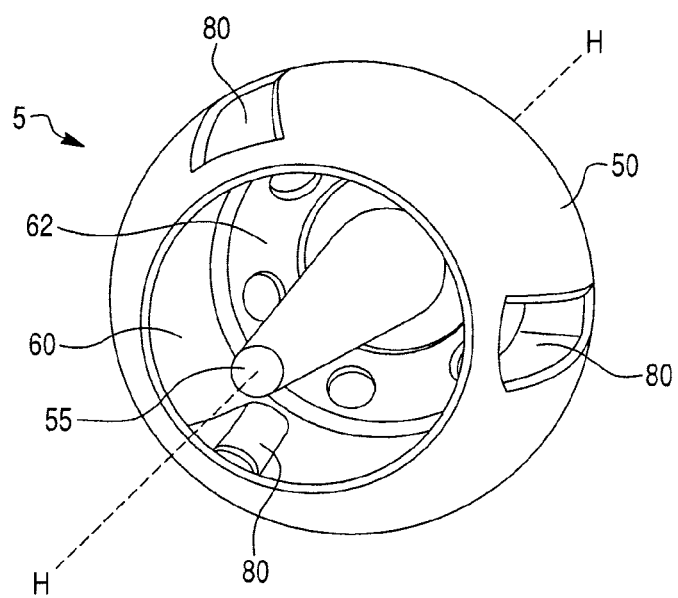

FIGS. 5A and 5B show an embodiment of a prosthetic device 5 according to the present invention. In this embodiment, the prosthetic device 5 is a femoral hip implant (e.g., a femoral head cup). The present invention, however, is not limited to hip implants. The prosthetic device may be any cup-shaped orthopedic joint implant, such as an implant for resurfacing a portion of a ball and socket joint (e.g., a hip or shoulder joint). In the alternative, the prosthetic device may be a trial of an implant. As used herein, the term cup-shaped means having a generally convex outer surface and a generally concave inner surface, though the surfaces need not be continuous and may include one or more flat portions.

As shown in FIGS. 5A and 5B, the prosthetic device 5 is substantially cup-shaped and includes an outer surface 50, an inner surface 60, and at least one reservoir 80. The prosthetic device 5 may optionally include a stem 55. The prosthetic device 5 is designed to replace a portion of a joint that includes first and second bones that articulate with one another. For example, the joint may include a bone, such as the femoral head 16 of the femur 14, and an opposite bone, such as the acetabulum 22 of the pelvis 12. As with a conventional hip resurfacing femoral implant (such as the femoral head cup 32 shown in FIG. 3C), the prosthetic device 5 is designed to be implanted on the femoral head 16 to restore functionality to the joint 10 in cases where the femoral head 16 is compromised, e.g., its surface is damaged or diseased.

FIGS. 6A-6D show another embodiment of the prosthetic device 5 according to the present invention. In this embodiment, the prosthetic device 5 is similar to the embodiment of FIGS. 5A and 5B except the prosthetic device 5 additionally includes at least one fluid passage 90, each in fluid communication with a corresponding reservoir 80, and a plurality of extension members 70.

Figure 2A:
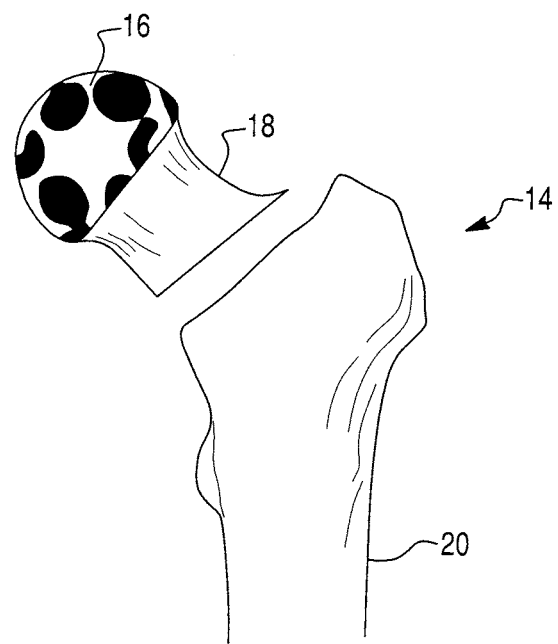
FIG. 2A is a perspective view of a bone cut made during a conventional total hip replacement procedure.
Figure 2B:
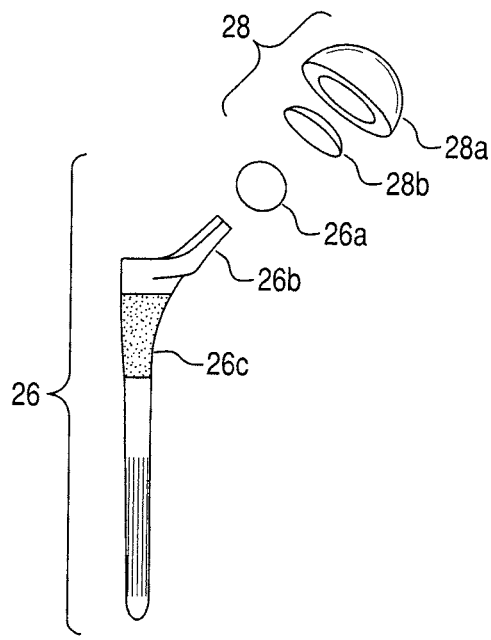
FIG. 2B is a perspective view of a femoral component and an acetabular component for a conventional total hip replacement procedure.
Figure 2C:
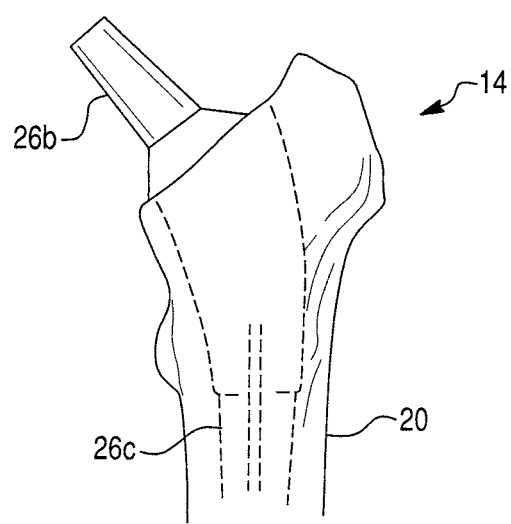
FIG. 2C is a perspective view of the femoral component of FIG. 2B implanted in a femur.
Figure 6A:
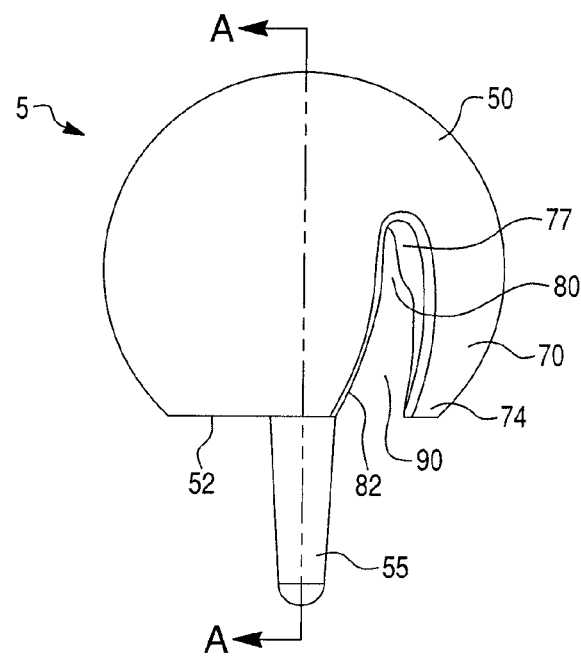
FIG. 6A is a perspective view of an embodiment of prosthetic device according to the present invention.

In the embodiments shown in FIGS. 5A, 5B, and 6A-6D, the outer surface 50 of the prosthetic device 5 is configured to replace the surface of the femoral head 16. Thus, the outer surface 50 forms one articular surface of the hip joint 10 when the prosthetic device 5 is implanted in a patient. The other articular surface is formed either by the opposite bone (i.e. the natural acetabulum 22) or by an acetabular component implanted in the opposite bone (such as the acetabular component 28 shown in FIG. 2B). The outer surface 50 preferably is convex and substantially shaped in the form of a sphere with the bottom portion of the sphere being truncated by a plane T-T (shown in FIGS. 5A and 6B) so that the outer surface 50 terminates at an edge (or rim) 52. The edge 52 is located at the base of the prosthetic device 5. An axis H-H passes through the geometric center of the sphere and is oriented to be perpendicular to the plane T-T. As noted above, the outer surface 50 need not be continuous. For example, the outer surface 50 may be interrupted by one or more of the reservoirs 80 (as shown in FIGS. 5A and 6A) and/or one of more of the fluid passages 90 (as shown in FIG. 6A). To promote articulation, the outer surface 50 can be manufactured with high sphericity and surface smoothness to minimize friction and wear in accordance with parameters known in the art. In this manner, the outer surface 50 is configured to operatively engage (or articulate with) at least one of a bone of the joint 10 (e.g., the opposite bone or acetabulum 22) and a component implanted in the joint 10 (e.g., the acetabular component 28).

The inner surface 60 of the prosthetic device 5 is separated from the outer surface 50 by a wall thickness t (shown in FIG. 6B) and, like the outer surface 50, terminates at the edge 52. As with the outer surface 50, the inner surface 60 need not be continuous. For example, the inner surface 60 may be interrupted by one or more of the reservoirs 80 and/or one of more of the fluid passages 90. At least a portion of the inner surface 60 is configured to connect to a bone of the joint 10. For example, the inner surface 60 may include a first portion 62 (shown in FIG. 6B), which is a bone-engaging surface that is adapted to connect to the femoral head 16 of the femur 14. For example, as shown in FIG. 7B, the first portion 62 may directly abut the bone and/or a cement mantle used to promote fixation of the prosthetic device 5. Because the first portion 62 engages the bone, the first portion 62 is preferably shaped to mate with the bone. Thus, as shown in FIG. 7B, the first portion 62 may have a shape that substantially corresponds to the shape of a prepared (i.e., cut or sculpted) bone. In cases where preparation is minimal or the natural bone is left intact, the shape of the first portion 62 can more closely match the natural surface geometry of the femoral head 16.

Figure 6B:
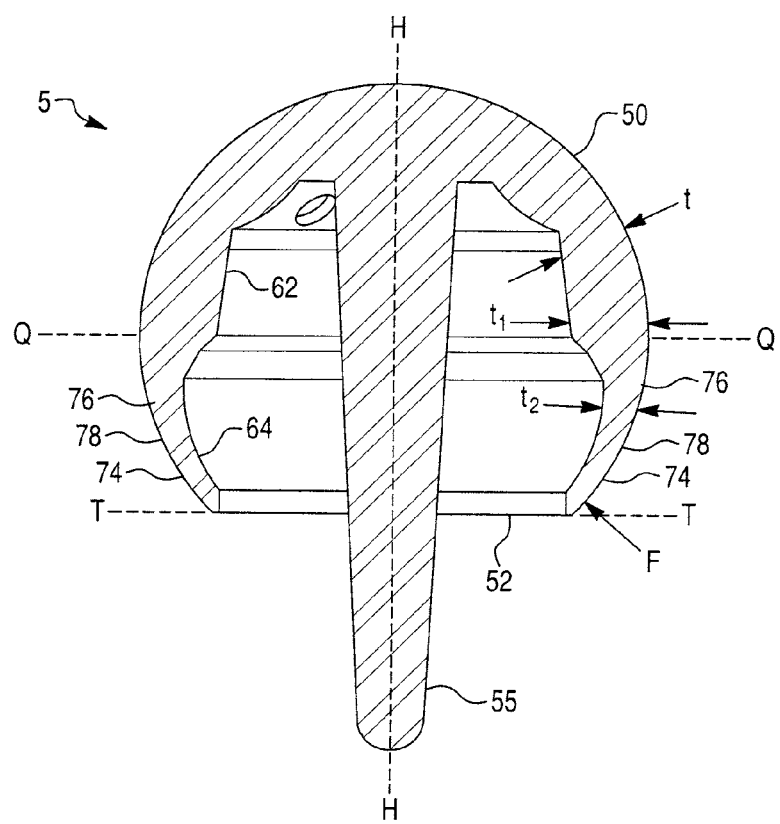
FIG. 6B is a cross sectional view of the prosthetic device of FIG. 6A taken along the line A-A.
Figure 6C:
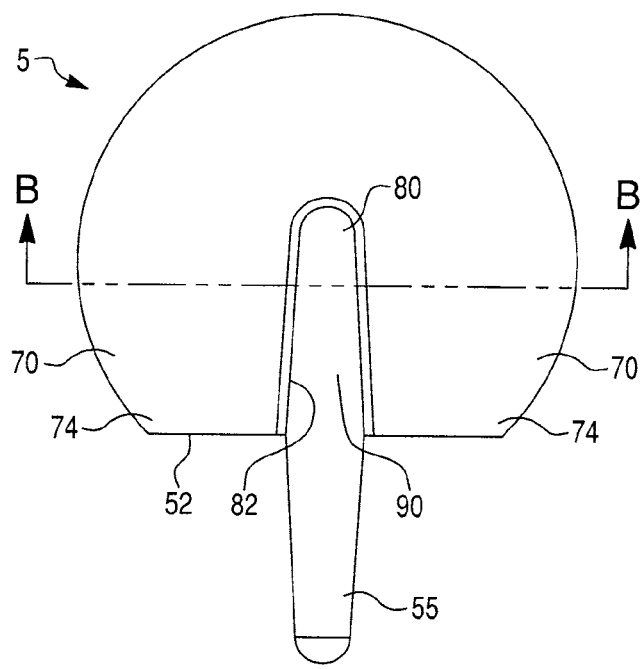
FIG. 6C is an elevation view of the prosthetic device of FIG. 6A.
Figure 7A:
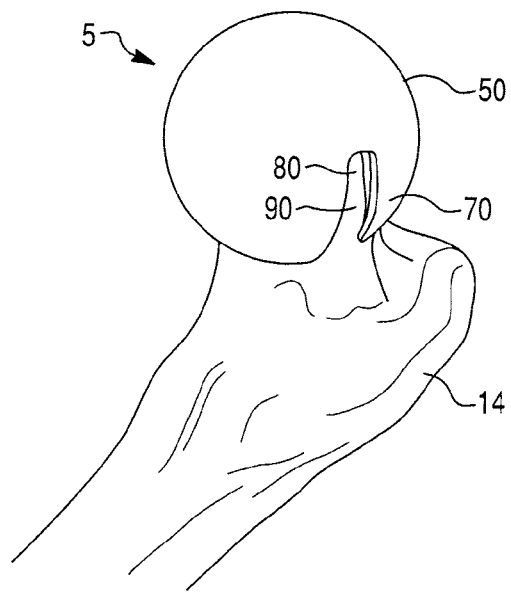
FIG. 7A is a perspective view of an embodiment of prosthetic device according to the present invention implanted on a femur.
Figure 7B:
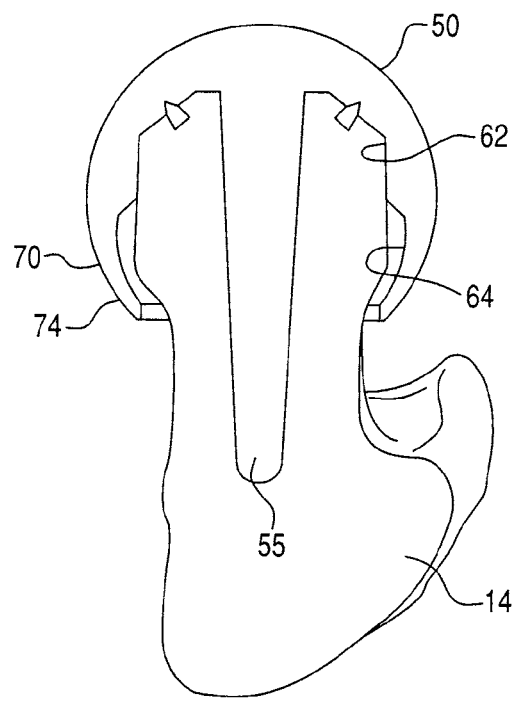
FIG. 7B is a cross sectional view of the prosthetic device of FIG. 7A.

The inner surface 60 may also include a second portion 64 (shown in FIG. 6B). In contrast to the first portion 62, the second portion 64 will not contact the femur 14 when the first portion 62 of the prosthetic device 5 is connected to the femur 14. Thus, as shown in FIG. 7B, when the prosthetic device 5 is implanted on the bone, the first portion 62 of the inner surface 60 connects to the bone while the second portion 64 is separated from the bone by a gap.

Figure 6D:
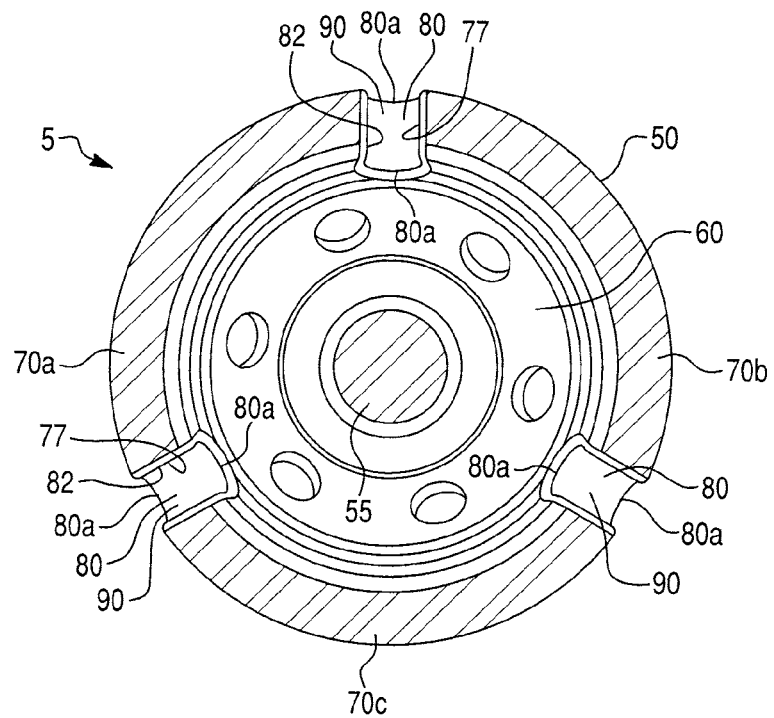
FIG. 6D is a cross sectional view of the prosthetic device of FIG. 6C taken along the line B-B.

The prosthetic device 5 also includes at least one reservoir 80. Thus, the prosthetic device 5 may include a single reservoir 80 or a plurality of reservoirs 80. As shown in FIGS. 5A and 5B, a reservoir 80 is a hole or aperture in the prosthetic device 5 that extends completely through the wall of the prosthetic device 5, preferably to permit fluid communication between a bone/component on one side with a bone/component on another side. For example, as best seen in FIG. 6D, a reservoir 80 has an opening 80a at each of the inner surface 60 and the outer surface 50 and extends therebetween. The edge or perimeter of the opening 80a at the outer surface 50 is preferably rounded to ensure smoothness of the outer surface 50 to minimize friction and wear during articulation.

The reservoirs 80 advantageously promote lubrication of the joint 10. In particular, the reservoirs 80 assist in the propagation of the synovial fluid 25a. For example, when the prosthetic device 5 is implanted in the joint 10, the synovial fluid 25a collects in the reservoirs 80. During articulation, the reservoirs 80 gather and distribute the synovial fluid 25a between the articulating components. Thus, the reservoirs 80 move the synovial fluid 25a around the joint 10 and between the femoral and acetabular components. As a result, joint lubrication is improved and friction and wear are reduced.

The prosthetic device 5 may further include at least one fluid passage 90 that is configured to permit fluid communication between a source of fluid (e.g., the synovial membrane 25) and the reservoir 80. For example, in the embodiment of FIG. 6A, the fluid passage 90 comprises an opening that extends from the base of the prosthetic device 5 to the reservoir 80 creating a channel or conduit that is open at the base of the prosthetic device 5 and that connects to the reservoir 80. This configuration enables the fluid passage 90 to channel or communicate the synovial fluid 25a generated by the synovial membrane 25 to the reservoir 80. In addition to functioning as a fluid conduit, the fluid passage 90 can also supplement the fluid distribution function of the reservoir 80 by gathering and distributing the synovial fluid 25a between the articulating components in the same manner as the reservoir 80. Thus, the fluid passage 90 further promotes lubrication of the joint 10. Similar to the reservoir 80, the fluid passage 90 preferably extends completely thorough the wall of the prosthetic device 5 so that it is open at both the inner surface 60 and the outer surface 50. Additionally, as with the reservoir 80, the edge or perimeter of the fluid passage 90 at the outer surface 50 is preferably rounded to ensure smoothness of the outer surface 50 to minimize friction and wear during articulation.

Figure 9:
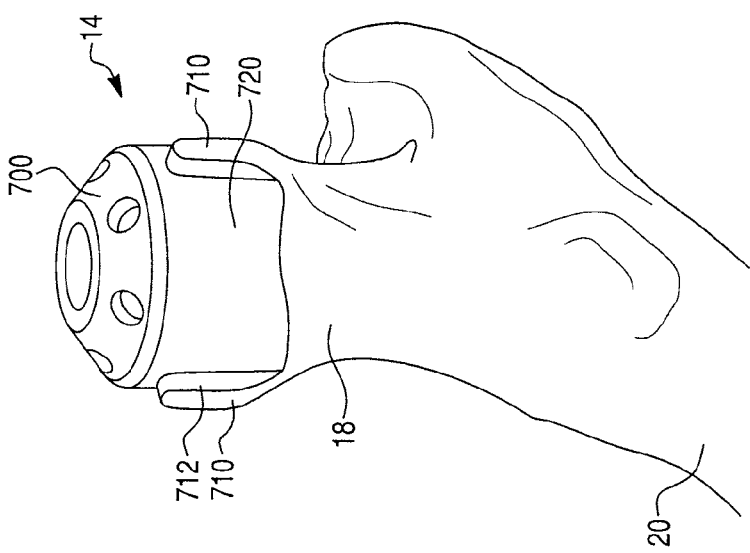
FIG. 9 is a perspective view of a sculpted femur according to the present invention.

Another advantage of the reservoirs 80 and the fluid passages 90 is that they provide an opening or passageway from the outer surface 50 of the prosthetic device 5 to the bone. As a result, the synovial fluid 25a can directly contact the femoral head 16, which is beneficial, at least in part, because the synovial fluid 25a is nutrient-rich and may inhibit the growth of bacteria. Additionally, the openings created by the reservoirs 80 and the fluid passages 90 reduce the amount of bone that must be resected to accommodate implantation of the prosthetic device 5. In particular, bone cuts can be eliminated or reduced on areas of the femur 14 where the reservoirs 80 and/or the fluid passages 90 will be disposed. For example, as shown in FIG. 9, the surgeon may sculpt the femur 14 such that the prepared bone includes one or more raised portions 710 that comprise uncut or minimally cut bone. As illustrated in FIG. 9, the shape of a perimeter 712 of a raised portion 710 may be similar to the shape of a perimeter (or border) 82 of the corresponding reservoir 80 and/or fluid passage 90. In operation, when implanting the prosthetic device 5, the surgeon can orient the prosthetic device 5 such that the raised portions 710 on the bone are aligned with the corresponding reservoirs 80 and fluid passages 90 of the prosthetic device 5. As described further below, the prosthetic device 5 can then be moved into position on the bone such that the raised portions 710 of the bone engage the corresponding reservoirs 80 and/or fluid passages 90 of the prosthetic device 5.

In an exemplary embodiment, during surgical planning, the surgeon can plan placement of the prosthetic device 5 on the patient's femoral head 16 such that at least one of the reservoirs 80 and/or the fluid passages 90 coincides at least partially with a critical region of the anatomy, such as a portion of the vascular region 24. As a result, during surgery, the surgeon can avoid cutting the bone in the designated region or can make only minimal bone cuts in the designated region. This advantageously decreases the amount of bone that must be resected in the designated region potentially resulting in improved preservation of critical structures (such as the retinacular vessels 24a) and reduced likelihood of femoral notching.

The reservoirs 80 and the fluid passages 90 are not limited in shape, size, or location but instead may have any shape, size, or location suitable for promoting fluid flow and/or preserving one or more designated regions of anatomy without degrading the strength and stability of the prosthetic device 5. Although the prosthetic device 5 preferably includes at least three equally spaced reservoirs 80 and/or fluid passages 90, the prosthetic device 5 may include more or fewer depending on the desired performance characteristics of the prosthetic device 5.

Figure 8:
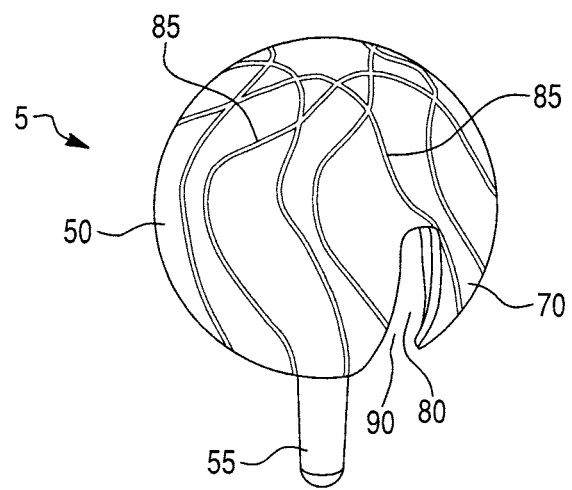
FIG. 8 is a perspective view of an embodiment of prosthetic device according to the present invention.

In one embodiment, the fluid passages 90 may be disposed on the outer surface 50 of the prosthetic device 5 meaning that they do not extend all the way through the wall of the prosthetic device 5. For example, as shown in FIG. 8, the outer surface 50 may include one or more fluid passages that are formed as channels 85. In this embodiment, the channels 85 can collect and distribute the synovial fluid 25a in a manner similar to the reservoirs 80. Unlike the reservoirs 80, however, the channels 85 are surface features and do not extend through the wall of the prosthetic device 5. Fluid passages disposed on the outer surface 50 are not limited to channels but may be any surface feature suitable for collecting and moving fluid, including any of the features described in U.S. Pat. No. 6,866,685, which is hereby incorporated by reference herein in its entirety.

The prosthetic device 5 may also include a plurality of extension (or deflection) members 70. As shown in FIGS. 6A and 6B, the inner and outer surfaces 60 and 50 extend to form the extension members 70. For example, as shown in FIG. 6B, the prosthetic device 5 includes an upper portion disposed above a plane Q-Q, and the inner and outer surfaces 60 and 50 extend below the plane Q-Q to form the extension members 70. Thus, in this embodiment, each extension member 70 extends below the plane Q-Q and has a distal end 74 that terminates at the base or edge 52 of the prosthetic device 5. Additionally, each extension member 70 preferably includes a neck region 76 located below the plane Q-Q and a body region 78 disposed below the neck region 76. As shown in FIG. 6B, the body region 78 includes the distal end 74 of the extension member 70. In the neck region 76, the wall thickness t of the prosthetic device 5 decreases or necks down. For example, a wall thickness $t_1$ taken at the plane Q-Q is greater than a wall thickness $t_2$ taken below the plane Q-Q. The location of the plane Q-Q may be adjusted (e.g., moved up or down) and may also be varied for each extension member 70 as desired. As shown in FIG. 6A, at least one reservoir 80 and/or at least one fluid passage 90 is disposed between adjacent extension members 70 to form an opening between the adjacent extension members 70. For example, as best seen in FIG. 6D, a first reservoir 80 and a first fluid passage 90 are disposed between adjacent extension members 70a and 70b; a second reservoir 80 and a second fluid passage 90 are disposed between adjacent extension members 70b and 70c; and a third reservoir 80 and a third fluid passage 90 are disposed between adjacent extension members 70c and 70a. Thus, a distal end 74 of each extension member 70 is separated from a distal end 74 of each adjacent extension member 70 by a reservoir 80 and/or a fluid passage 90.

The separation between extension members 70, in combination with the decreased wall thickness t, imparts compliance to the extension members 70. As a result, the extension members 70 have the ability to flex or deflect in response to a force (such as a force F shown in FIG. 6B) that acts on the outer surface 50 of the prosthetic device 5. Thus, each adjacent extension member 70 includes a distal end 74 and at least a portion that is configured to flex (i.e., a flexible portion) upon application of a joint force (e.g., the force F) such that the distal end 74 is displaced. The flexible portion may include, for example, the neck region 76 and/or the body region 78. Additionally, because the extension members 70 are separated, the extension members 70 can flex independently of one another. In this manner, the flexible portion of one extension member 70 is configured to flex at least partially independently of the flexible portion of each adjacent extension member 70. To select an implant having an appropriate degree of compliance, a surgeon can measure a patient's ability to generate side force by adducting and abducting the leg prior to surgery and measuring the result with a force gauge. This information can then be used in the implant planning process to identify the implant that is most suitable for the patient. A range of implants may be provided with varying degrees of stiffness. For example, in one embodiment, a low flex implant can be configured to deflect upon application of about 20 lbs of force, a medium flex implant can be configured to deflect upon application of about 12 lbs of force, and a high flex implant can be configured to flex upon application of about 6 lbs of force.

Figure 7C:
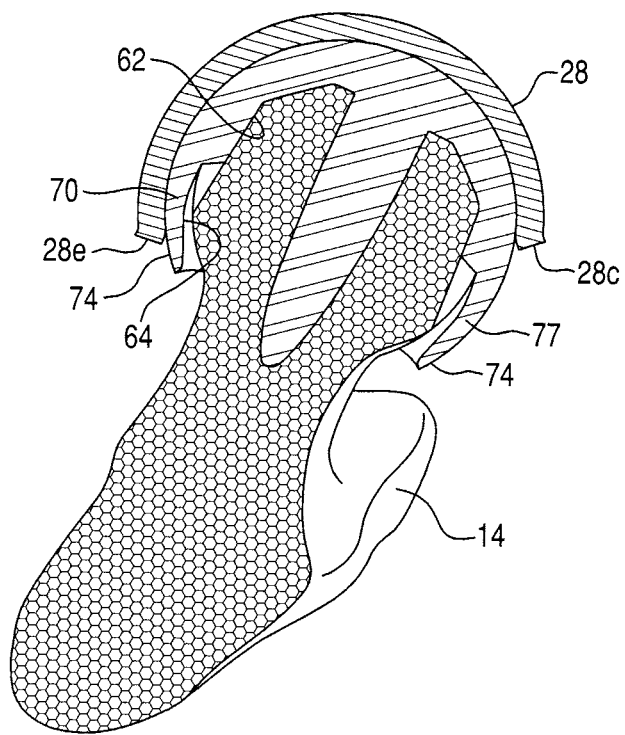
FIG. 7C is a cross sectional view of the prosthetic device of FIG. 7A showing the prosthetic device engaged with an acetabular component.

When the bone is sculpted and the prosthetic device 5 is implanted on the bone, the extension members 70 are separated from the bone by a gap. For example, as shown in FIGS. 7B and 7C, the inner surface 60 at the extension members 70 includes the portion 64, which, as discussed above, does not contact the femur 14 when the prosthetic device 5 is implanted on the femur 14. The lack of contact is due, at least in part, to the thinner wall thickness t of the extension members 70. In this manner, each extension member 70 is configured such that the extension member 70 will not contact the bone when the inner surface 60 is connected to the bone. Because the extension members 70 are separated from the bone, the extension members 70 have room to flex inward toward the bone. In operation, when a joint force (e.g., the force F) is applied to the outer surface 50 of an extension member 70, the extension member 70 can flex such that the distal end 74 is displaced at least partly into the gap.

Using techniques known in the art, the wall thickness t along the length of a particular extension member 70 may be designed to provide the desired degree of flex based on predicted joint forces in the vicinity of the particular extension member 70 and the geometry and material properties of the prosthetic device 5. One design constraint, however, is that the wall thickness t must still be sufficiently thick (even in the thinner regions) to avoid micromotion, metal fatigue, and permanent deformation of the outer surface 50. Additionally, the wall thickness t must be sufficiently robust to provide good stress transfer, avoiding stress shielding (which can lead to bone loss) and excessive stress.

In a preferred embodiment, the upper portion of the outer surface 50 (e.g., the portion above the plane Q-Q) comprises a hemisphere, and the extension members 70 extend below the hemisphere. Additionally, as shown in FIG. 6B, the outer surface 50 at each extension member 70 preferably has a substantially spherical shape. As a result, the spherical curvature of the outer surface 50 is extended substantially below the plane Q-Q, which increases the articular contact area of the prosthetic device 5. In contrast, the outer surface of conventional femoral hip resurfacing components (such as the femoral head cup 32 shown in FIG. 3C) may not extend as far below the plane Q-Q and/or may have a different curvature below the plane Q-Q resulting in an outer surface that is more bell-shaped than spherical, potentially resulting in reduced contact area. One advantage of the increased contact area of the prosthetic device 5 is that, as the joint 10 moves through a range of motion, the outer surface 50 of the prosthetic device 5 may tend to remain in contact with a majority of or the entire opposing articular surface, i.e., the articular surface of either the natural acetabulum 22 or an acetabular component 28 implanted on the acetabulum 22. For example, in an exemplary embodiment shown in FIG. 7C, as the joint 10 moves through the range of motion, the distal ends 74 of the extension members 70 do not traverse (or articulate above) a rim (or edge) 28e of the acetabular component 28. In this manner, the prosthetic device 5 is configured to maintain substantial contact between the articular surface of the prosthetic device 5 (i.e., the outer surface 50) and the opposing articular surface throughout the range of motion. As a result, the prosthetic device 5 has improved load-bearing capability, including the ability to accommodate a larger acetabular component 28, as well as a stronger mechanical piston effect. As discussed above, a strong piston effect aids in preventing joint dislocation by generating a high vacuum in response to a force that attempts to extract the femur 14 from the acetabulum 22.

One advantage of the extension members 70 is reduced potential for lever arm dislocation. This is due, at least in part, to the ability of the extension members 70 to deflect combined with the increased articular contact area of the prosthetic device 5. For example, as discussed above and shown in FIGS. 4A-4D, lever arm dislocation may occur with a conventional hip implant at the extreme range of motion when the femoral neck impinges on the rim of the acetabular cup creating a lever arm that forces the femoral ball out of the acetabular cup. In contrast, as shown in FIG. 7C, the increased articular contact area of the prosthetic device 5 results in the extension member 70 (as opposed to the femoral neck 18) contacting a rim 28e of the acetabular component 28. Because the extension member 70 is compliant, a hard lever arm is not created. Instead, the extension member 70 flexes in response to the joint force. As a result, the potential for lever arm dislocation is reduced.

In one embodiment, one or more of the extension members 70 may include an anti-rotation feature configured to impart rotational stability to the prosthetic device 5 when the prosthetic device 5 is implanted on the bone. For example, as shown in FIG. 6A, the anti-rotation feature may comprise a wall (or surface) 77 of the extension member 70 that borders the reservoir 80 and/or the fluid passage 90. Thus, the wall 77 coincides with the perimeter 82 of the reservoir 80 and/or the fluid passage 90. In operation, when the prosthetic device 5 is implanted on the bone and a reservoir 80 and/or a fluid passages 90 is engaged with a corresponding raised portions 710 of the bone (as discussed above), the perimeter 712 of the raised portion 710 abuts the wall 77 thereby preventing rotation of the prosthetic device 5 on the femoral head 16.

Figure 3A:
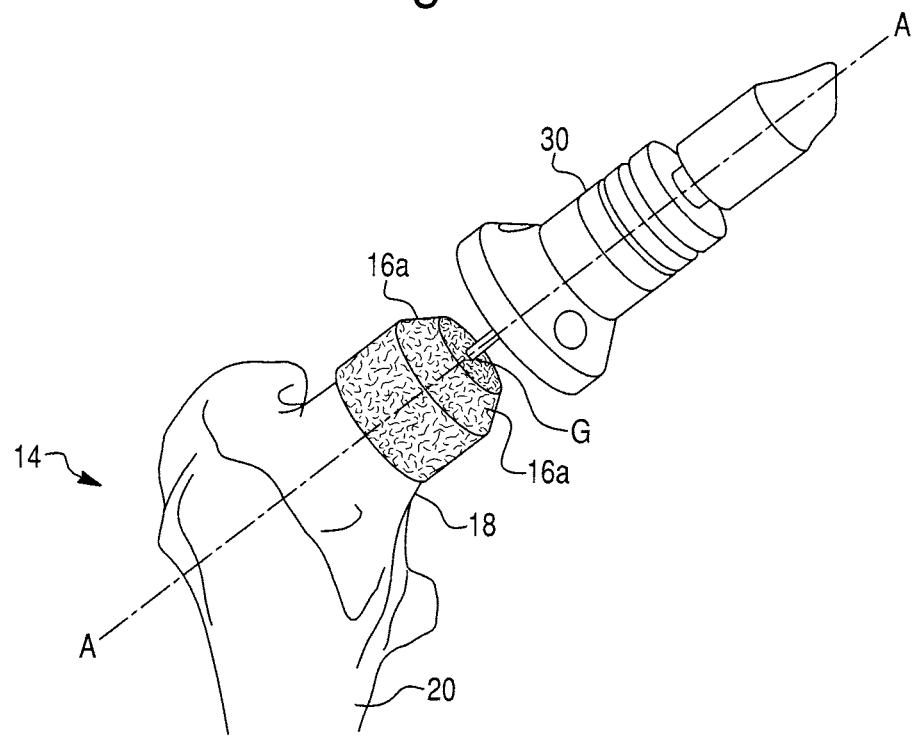
FIG. 3A is a perspective view of rotationally symmetric bone cuts made with a cylindrical reamer during a conventional hip resurfacing procedure.
Figure 3B:
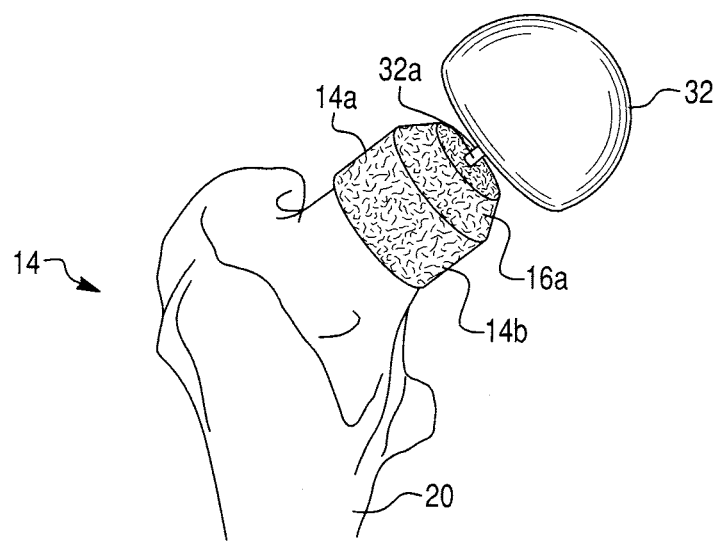
FIG. 3B is a perspective view of a femoral component for a conventional hip resurfacing procedure.
Figure 3C:
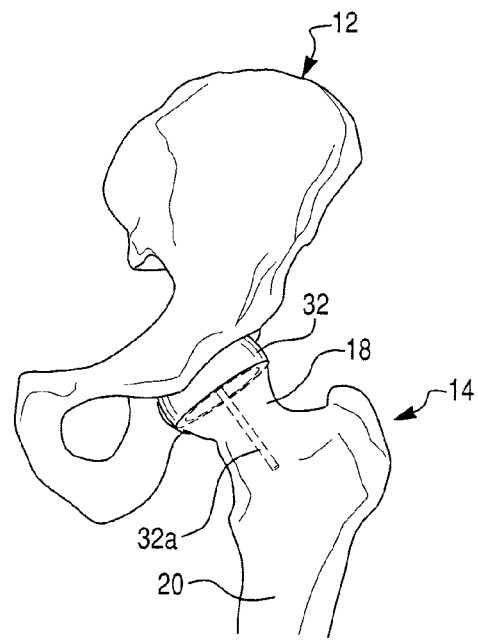
FIG. 3C is a perspective view of the femoral component of FIG. 3B implanted on a femur of a hip joint.
Figure 3D:
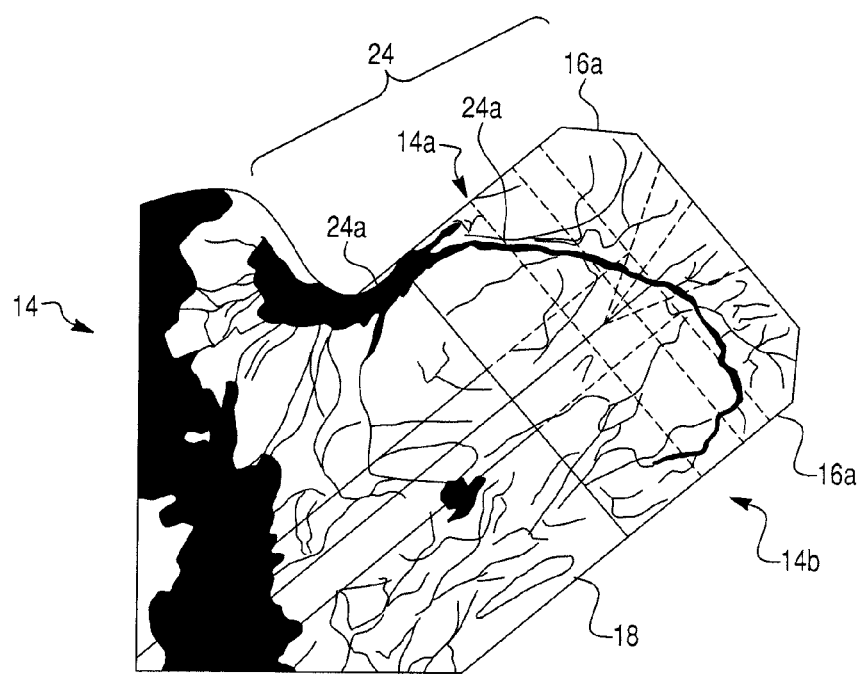
FIG. 3D is an illustration depicting the vascular region of FIG. 1B in relation to rotationally symmetric bone cuts made with a cylindrical reamer during a conventional hip resurfacing procedure.
Figure 4A:
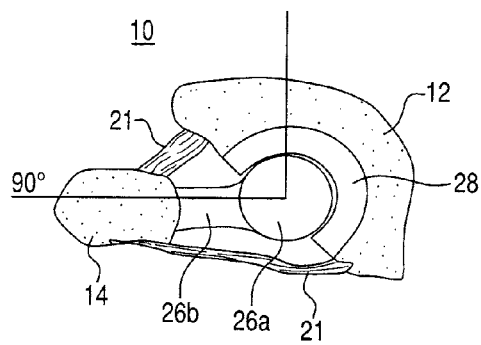
FIGS. 4A to 4D illustrate the mechanics of lever arm hip dislocation.
Figure 4B:
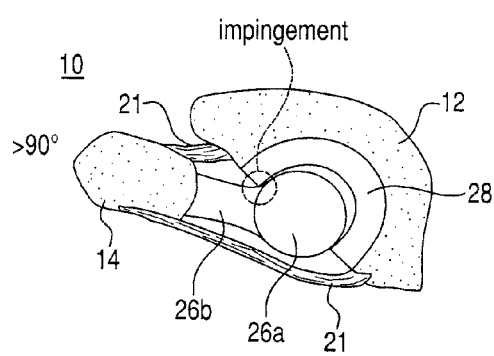
Figure 4C:
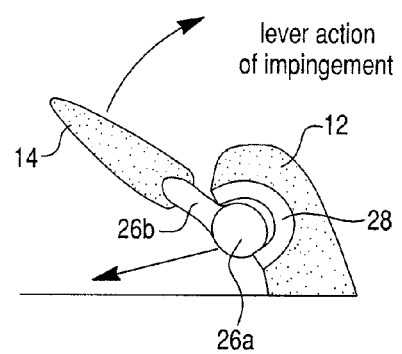
Figure 4D:
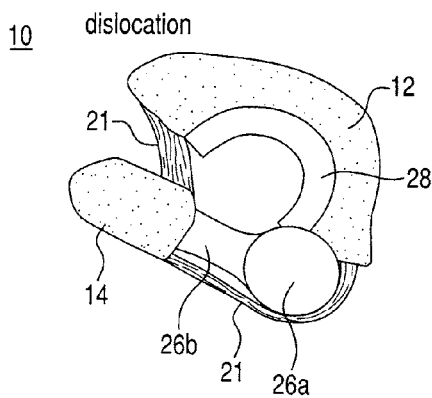

As shown in FIGS. 6A-6D, the prosthetic device 5 may include a stem 55 projecting from the inner surface 60 to aid in stability and initial fixation. The stem 55 may be formed integrally with the prosthetic device 5 or manufactured separately and connected to the prosthetic device 5 via mechanical means, such as screw threads or a press fit, as is known in the art. The stem 55 may be coaxial with the axis H-H (as shown in FIG. 6B) or offset from the axis H-H (as disclosed, for example, in U.S. Patent Application Pub. No. US 2003/0163202, which is hereby incorporated by reference herein in its entirety). Inclusion of the stem 55 on the prosthetic device 5 is optional. One reason the stem 55 may be omitted is because the bone preparation process for the prosthetic device 5 does not require use of a cylindrical reamer. As explained above in connection with FIG. 3A, use of a cylindrical reamer requires the surgeon to create a guide hole G in the femoral head 16 to center the reamer 30. The guide hole G is then filled by the stem 32a of a conventional femoral hip resurfacing implant (as shown in FIGS. 3B and 3C). As discussed further below, because the present invention does not require the use of a cylindrical reamer to prepare the bone, a guide hole (and corresponding stem to fill the guide hole) are not necessary. It may be desirable, however, to retain the stem 55 to ensure proper bone fixation, to ensure proper stress transfer to the bone, and/or to ease placement of the implant on the bone.

The inner surface 60 of the prosthetic device 5 may be designed to be fixed to the femur 14 in any known manner. For example, the prosthetic device 5 may be adapted to be cemented in place with bone cement (e.g., polymethylmethacrylate or PMMA) or press fit onto the bone without cement. For cemented designs, portions of the inner surface 60 that will be cemented to the bone (e.g., the portion 62) are preferably adapted to bond with the cement and may include cement pockets (e.g., shallow channels or circumferential grooves) to improve fixation, as is known in the art. For press fit designs, uncemented portions of the inner surface 60 (e.g., the portion 62) are preferably adapted to encourage the in-growth of bone to improve fixation. For example, such surfaces may be textured or roughened and/or may include a coating configured for bone in-growth, as is known in the art. The coating may be a porous coating, such as a sintered bead coating, a mesh coating, or plasma spray. Additionally or alternatively, the coating may be a bioactive coating, such as hydroxyapatite (HA).

The inner surface 60 of the prosthetic device 5 may also include other features adapted to promote fixation of the prosthetic device 5 to the femur 14. Such features may include one or more projections on the inner surface 60, such as pegs, spikes, fins, and the like, as known in the art. Such projections may be used with or without the stem 55. In one embodiment, the inner surface 60 includes a plurality of small projections (e.g., small, short pegs) and omits the larger and longer stem 55. Omission of the stem 55 in combination with a plurality of shallower fixation features advantageously provides fixation without significantly disrupting the internal vascular structures and bony anatomy of the femoral head 16.

The prosthetic device 5 may be made of any material suitable for use in orthopedic implant applications. For example, the prosthetic device 5 may include a biocompatible metal (e.g., a cobalt-chromium alloy, a titanium alloy, a zirconium alloy, stainless steel, or tantalum); a strong ceramic (e.g., an alumina or zirconia-based ceramic); one or more high performance polymers (e.g., UHMWPE); and/or a polymer composite. Additionally, selection of an appropriate material requires consideration of the specific design of the prosthetic device 5 (e.g., via finite element analysis, etc.) to ensure that the material has sufficient mechanical properties, in accordance with parameters known in the art. For example, in regions where the wall thickness t of the prosthetic device 5 is thin, a biocompatible metal may be more mechanically sound than a ceramic or polymer.

In operation, the prosthetic device 5 is implanted on the femur 14 of the patient after the surgeon has sculpted the femur 14. To ensure that the prosthetic device 5 can be properly implanted, the femoral head 16 (shown in FIG. 9) is preferably sculpted to have a surface 700 that is shaped to mate with the inner surface 60 of the prosthetic device 5 and one or more surfaces 720 configured to be separated from the inner surface 60. In particular, the surface 700 is shaped to mate with the bone-engaging portion 62 of the inner surface 60, as shown, for example, in FIGS. 7B and 7C. In contrast, a surface 720 is configured to be disposed opposite the portion 64 of the inner surface 60 and to be separated from the portion 64 by a gap. As discussed above, the gap ensures that the corresponding extension member 70 has room to flex or deflect. Thus, the surfaces 720 are sculpted to have a profile that provides sufficient clearance to accommodate displacement of the distal ends 74 of the associated extension members 70. The sculpted surface of the femoral head 16 may also include one or more raised portions 710. As mentioned above, the raised portions 710 result in improved bone conservation and can also engage the reservoirs 80 and/or the fluid passages 90 to impart rotational stability to the prosthetic device 5.

Various methods can be used to prepare the bone. For portions of the bone that will be sculpted into rotationally symmetric shapes, the surgeon can use a conventional cylindrical reamer (e.g., as shown in FIG. 3A). For example, in the embodiment shown in FIG. 9, the surgeon can cut the surface 700 of the femur 14 with a cylindrical reamer. When using the cylindrical reamer 30, however, care should be taken not to impinge upon the area of the bone that will include the raised portions 710. If the sculpted bone will not include the raised portions 710, the surface 720 can also be cut with a cylindrical reamer. In contrast, if the surgeon needs to sculpt the raised portions 710, conventional rotational cutting tools (such as the cylindrical reamer) cannot be used to cut this portion of the bone because the raised portions 710 and the surfaces 720 have a rotationally asymmetric shape, as shown in FIG. 9. Thus, the surgeon must utilize bone preparation techniques that enable the surface of the bone to be sculpted into customized, rotationally asymmetric shapes.

One method of customized bone preparation includes freehand sculpting where the surgeon uses a freehand technique to sculpt the bone with a high speed burring device. Freehand sculpting, however, is challenging and requires a high degree of surgical skill. In a true freehand technique, the surgeon sculpts the bone with the burr in an unaided manner. To improve execution of bone cuts, the surgeon can utilize mechanical guides, cutting jigs, and/or templates. Additionally or alternatively, the surgeon can use a tracked cutting tool and a computer assisted surgery system that provides visual and/or audible guidance during cutting. The cutting tool could also be controlled to be retracted and/or disabled if the cutting tool is moved beyond a defined cutting boundary.

Another method of preparing the bone includes using an autonomous robotic system with a high speed burr to perform bone cuts automatically. Although such systems enable precise bone resections for improved implant fit and placement, they act autonomously and thus require the surgeon to cede a degree of control to the robot. Additional drawbacks include the large size of the robot, poor ergonomics, need to rigidly clamp the bone during registration and cutting, increased incision length for adequate robot access, and limited acceptance by surgeons and regulatory agencies due to the autonomous nature of the system.

Another method of preparing the bone includes using a haptically guided interactive robotic system, such as the haptic guidance system described in U.S. patent application Ser. No. 11/357,197 (Pub. No. 2006/0142657), filed Feb. 21, 2006, and hereby incorporated by reference herein in its entirety. As the surgeon manipulates a robotic arm to cut bone with a high speed burr, the system provides force feedback (i.e., haptic or tactile guidance) to guide the surgeon in sculpting the bone into the appropriate shape, which is pre-programmed into the control system of the robotic arm. In a preferred embodiment, the interactive robotic system is the TACTILE GUIDANCE SYSTEM™ currently manufactured by MAKO Surgical Corp., Fort Lauderdale, Fla. In one embodiment, the bone may be prepared as described in U.S. patent application Ser. No. 12/330,271 (U.S. Publication No. 2009/0149965), filed Dec. 8, 2008, by Arthur E. Quaid, titled PROSTHETIC DEVICE AND SYSTEM FOR PREPARING A BONE TO RECEIVE A PROSTHETIC DEVICE, and hereby incorporated by reference herein in its entirety.

Figure 10:
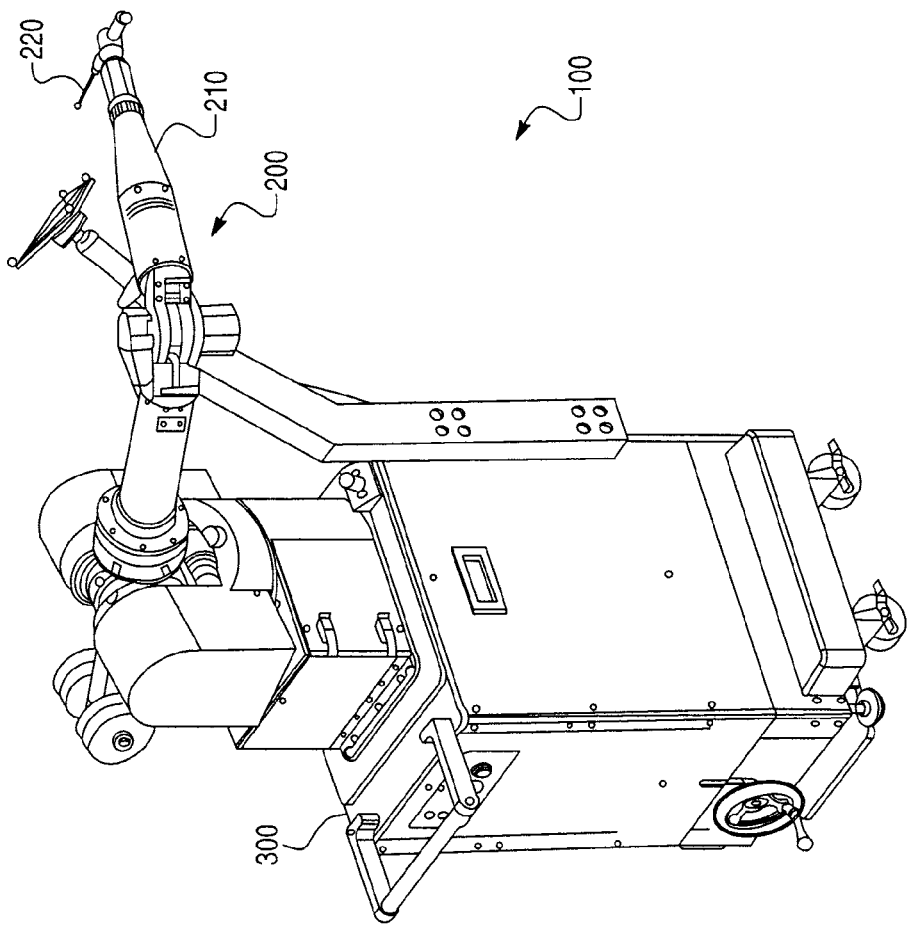
FIG. 10 is a perspective view of a surgical robotic system.

According to an exemplary embodiment, the femur 14 is prepared using a robotic system 100. As shown in FIG. 10, the robotic system 160 includes a guide structure 200 and a control system 300 for controlling the guide structure 200.

The guide structure 200 is configured to guide cutting of the bone into a shape for receiving the prosthetic device 5. The guide structure 200 comprises an articulated arm 210 with a distally mounted cutting tool 220 (e.g., a surgical burr). The guide structure 200 also incorporates a feedback mechanism (not shown) that includes a drive system comprising one or more actuators (e.g., motors) and a mechanical transmission. The feedback mechanism is configured to generate and convey force feedback to a user of the robotic system 100 to guide the user in making bone cuts. In operation, the surgeon cuts bone by grasping and manipulating the guide structure 200 (e.g., the arm 210 and/or the cutting tool 220) to make the desired bone cuts with the tool 220. During the cutting operation, the control system 300 controls the feedback mechanism to provide force feedback (e.g., haptic or tactile guidance) that guides the surgeon in executing the bone cuts. For example, the feedback mechanism may provide force feedback that tends to constrain the surgeon from penetrating a predefined virtual cutting boundary with the cutting tool 220. As discussed more fully below, the virtual cutting boundary may be defined by a bone-cutting pattern having a shape that corresponds to the desired shape of the sculpted bone. To enable the control system 300 to know the position of the bone-cutting pattern relative to the bone being cut, the bone-cutting pattern is registered to the patient's anatomy using any known registration technique. In this manner, the guide structure 200 is configured to guide cutting of the bone into a shape suitable for receiving the prosthetic device 5.

The control system 300 controls the robotic system 100, including the feedback mechanism of the guide structure 200. The control system 300 may be, for example, a computing system for controlling a haptic device as described in the above-referenced U.S. Patent Application Pub. No. 2006/0142657. To guide the surgeon in preparation of the bone, the control system 300 defines a virtual cutting boundary that is registered to the anatomy of the patient and then controls the feedback mechanism to provide force feedback to the surgeon to prevent the surgeon from making bone cuts that violate the virtual cutting boundary, as described, for example, in the above-referenced U.S. Patent Application Pub. No. 2006/0142657. The cutting boundary may be defined by a bone-cutting pattern programmed into the control system 300. For example, the bone-cutting pattern may be a haptic object or geometric model as described in the above-referenced U.S. Patent Application Pub. No. 2006/0142657. The bone-cutting pattern may be a single pattern that defines a final surface shape of the prepared bone or may comprise a plurality of patterns defining a plurality of bone cuts to be made to achieve the final surface shape. As discussed above, the shape of the bone-cutting pattern corresponds to the desired shape of the sculpted bone. During bone cutting, the control system 300 controls the feedback mechanism to provide force feedback guidance to the surgeon to enable the surgeon to maintain the cutting tool 220 within the cutting boundary defined by the bone-cutting pattern. As a result, the surface of the bone is sculpted into the shape defined by the bone-cutting pattern.

Figure 11:
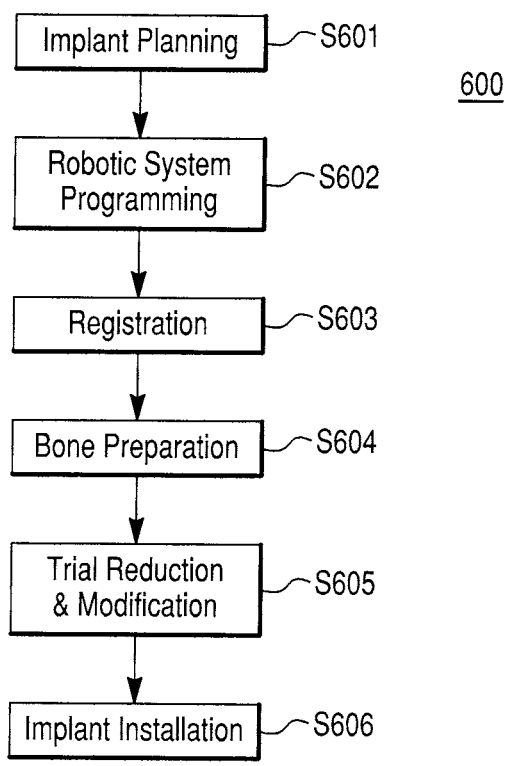
FIG. 11 is a diagram of an embodiment of a surgical method according to the present invention.

An embodiment of a surgical method 600 according to the present invention is illustrated in FIG. 11. In step S601 (Implant Planning), the surgeon selects a prosthetic device 5 to be implanted in the patient and plans where the prosthetic device 5 will be placed relative to the patient's anatomy. Implant planning may be accomplished preoperatively or intraoperatively and adjusted as necessary at any time. As is well-known, planning may be image-based or imageless in two or three dimensions (2D or 3D). For accuracy reasons, 3D image-based planning is preferred.

For 3D image-based planning, 3D images of the patient's bones are acquired using any suitable 3D imaging technology, such as CT, MRI, ultrasound, functional imaging, or other noninvasive or semi-invasive 3D imaging technology. The acquired image is processed using well known image processing techniques to generate 3D models of the bones of the joint. Alternatively, for 3D imageless planning, bone atlases may be used to obtain the 3D bone models. A bone atlas is a statistical model that represents the relevant anatomy, including information on natural variations typically existing in specific populations with specific distributions and probabilities. Using well known image processing techniques and statistical data, the bone atlas may be transformed or "morphed" to find a best fit to the patient's anatomy based on known demographic information, such as gender, age, stage of disease, and other patient-specific characteristics. Additionally, although preoperative planning can be accomplished using the initial bone atlas model, once intraoperative registration data on the actual bones is obtained, the bone atlas can be further morphed to improve the fit to the patient's anatomy along with corresponding adjustments to the implant plan.

After obtaining 3D bone models (image-based or imageless), the surgeon can use the models to plan placement of the prosthetic device 5 in the joint to achieve the desired clinical outcome. Various factors may be considered during implant planning, such as leg length, joint biomechanics, and joint kinematics, including range of motion, joint motion correction, impingement considerations, deformities, and the like. Implant planning may also take other factors into consideration, such as bone quality (e.g., measured using bone densitometry techniques), vascular structures in joint (e.g., the vascular region 24), existing necrotic tissue of the bone, prior joint trauma (including surgery), pre-existing implants, specific implant design features, and the like. Implant planning may be accomplished in any known manner, such as by manually positioning a virtual model of the implant (e.g., the selected prosthetic device 5) relative to the 3D model of the bone (e.g., the femur 14), as described in the above-referenced U.S. Patent Application Pub. No. 2006/0142657. The 3D nature of the application advantageously enables the surgeon to use simple image manipulation techniques to manually place implant components on the bone model, manipulate the implant components to obtain the appropriate position and alignment, and assess how the implant components will perform when installed in the joint.

An additional advantage of 3D image-based planning is the ability to analyze the level of damage and deformity of the diseased joint relative to itself as well as to the contralateral joint. For example, in the event the contralateral side is undamaged or in a reasonably healthy condition, the surgeon may consider the contralateral side as the goal for implant planning. For example, during implant planning, the surgeon can transpose an image of the healthy contralateral side to the image of the diseased side and use the healthy contralateral image as a reference target for planning implant placement.

In one embodiment, implant planning is accomplished by obtaining 3D bone models of the pelvis 12 and the femur 14. If only the femoral head 16 is being resurfaced, the surgeon plans the position of the prosthetic device 5 (i.e., the femoral component) on the model of the femur 14 (e.g., using the implant planning procedure described in the above-referenced U.S. Patent Application Pub. No. 2006/0142657). If the acetabulum 22 is also being resurfaced, the surgeon also plans the position of the acetabular component 28 on the model of the pelvis 12. Appropriate placement involves more than simply positioning models of the implant components on the bone models. As is well known, the surgeon must consider other factors, including the degree of post operative joint range of motion, whether the planned placement of the implants will result in proper leg length, and whether the thickness of the bone remaining in the acetabulum 22 after the acetabulum 22 is sculpted is structurally sufficient. For example, because the acetabulum 22 is relatively thin, placement of the acetabular component 28 should be as shallow as possible. Thus, in one embodiment, the position of the acetabular component 28 is planned first, and the position of the femoral component (e.g., the prosthetic device 5) is then planned to match the position of the acetabular component 28.

Positioning the prosthetic device 5 on the femoral head 16 should also take into account the patient's proper leg length. For example, if a patient has a healthy right hip joint and a left hip joint with a worn femoral head 16, the patient's left leg will be shorter than the right leg. Thus, when planning the placement of implant components in the left hip joint, the surgeon should ensure that the planned implant placement will achieve the correct leg length (i.e., the left leg should match the right leg). Because the patient's preoperative leg length is incorrect, however, proper leg length must be estimated. One way to estimate proper leg length is to align the patient's feet on the examination table and capture relative positions of the pelvis 12 and the femur 14. Another way to estimate leg length is to use the anatomically intact contralateral joint as mentioned above. Either approach should provide a nominal gap between the acetabulum 22 and the femoral head 16 that will result in comparable leg lengths. Implant placement can then be planned to achieve this nominal gap.

Another factor to consider during implant planning is the rotational alignment or orientation of the prosthetic device 5 on the femoral head 16. For example, the prosthetic device 5 is preferably oriented based on anticipated impingement contact. For example, the prosthetic device 5 can be oriented so that, at the extreme range of motion, at least one extension member 70 will be impinged by the rim of the acetabular component or the natural acetabulum. As discussed above, the impinged extension member 70 deflects in response to an applied force F thereby reducing the potential for lever arm dislocation. In an exemplary embodiment, the prosthetic device 5 is arranged on the femoral head 16 so that one extension member 70 is facing in the medial direction and one extension member 70 is facing in the lateral direction. In operation, when the patient adducts the leg to the point of impingement, the medially-oriented extension member 70 comes into contact with the edge of the acetabular component and deflects instead of creating a hard lever arm. Similarly, when the patient abducts the leg to the point of impingement, the laterally-oriented extension member 70 comes into contact with the edge of the acetabular component and deflects instead of creating a hard lever arm. To ensure that the prosthetic device 5 is properly oriented, the prosthetic device 5 can include locating features disposed on the inner surface 60 that are keyed to the sculpted geometry of the bone surface. For example, in one embodiment, the inner surface 60 of the prosthetic device 5 includes one or more holes (and/or projections) configured to engage with corresponding projections (and/or holes) that are sculpted on the surface of the femoral head 16. When the surgeon aligns the locating features with the corresponding sculpted geometry of the bone, the prosthetic device 5 is automatically arranged in the proper orientation for impingement contact.

Alternatively, implant planning (or portions thereof) can be automated instead of manual. For example, 3D imaging in combination with programmable implant planning guidelines can enable a computer assisted surgery system to automatically plan the placement of implant components based on, for example, a recommended surgical technique, implant specific design, and/or patient joint condition. Once automatic planning occurs, the software can perform a virtual simulation of the joint in motion to provide the surgeon with information on joint kinematics and biomechanics as well as expected loads on the joint.

Figure 1B:
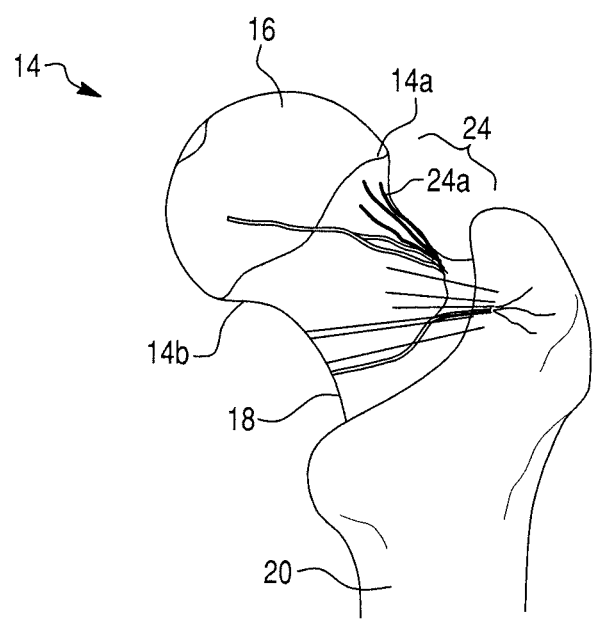
FIG. 1B is an illustration depicting a vascular region of a femur.
Figure 1C:
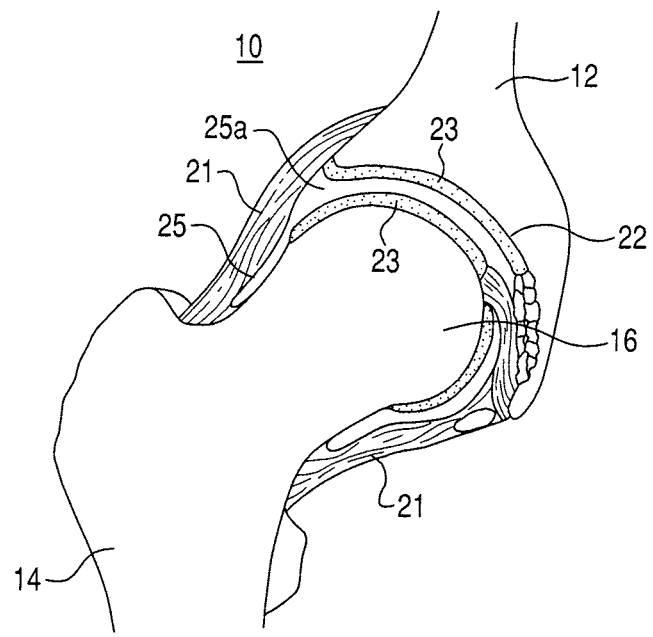
FIG. 1C is an illustration of a hip joint formed by the femur and pelvis of FIG. 1A.

Although 3D imaging is preferred, 2D imaging may also be used. For example, as can be seen in FIGS. 1A through 1C, the hip joint 10 is a ball and socket joint with fairly simple anatomical shapes (as compared, for example, to a knee or ankle joint). The simple anatomy of the hip joint 10 combined with substantially symmetric geometry on the anterior/posterior plane for the femur 14 and substantially symmetric anatomy on the medial/lateral plane for the acetabulum 22 enables accurate planning of implant placement based on 2D images and implant models. The 2D implant planning process may utilize 2D templating techniques, as is well known. Alternatively, a 2D image may be used to find a best fit to an existing bone model, such as the bone atlas described above or other models representing the joint anatomy. For example, using well known image processing techniques, a computer can determine a best fit between 2D images of the patient's bone and the atlas and then morph the atlas to have a best fit to the specific information in the 2D image (e.g., size, shape, morphology, disease stage, etc.). Once the atlas is morphed to represent the specific patient anatomy, the atlas can be used to plan implant placement.

As described above, implant planning may be manual, automated, or a combination of manual and automated techniques. Additionally, implant planning may be performed preoperatively or intraoperatively and adjusted as necessary at any time. For example, a surgeon who chooses to plan implant placement preoperatively can make final adjustments to or even completely revise the plan intraoperatively after determining the actual condition of the joint. One disadvantage of preoperative planning, however, is that images of the patient must be acquired preoperatively and then registered to the actual patient during the surgical procedure. In contrast, with intraoperative planning, imaging is performed intraoperatively thereby avoiding the burden of preoperative imaging. Additionally, for certain imaging modalities, if the imaging apparatus is properly calibrated and both the imaging apparatus and the patient are tracked at the time the images are acquired, the acquired images are automatically registered with the patient. This eliminates the need for manual registration and thus results in a significant time savings for the surgeon. Any suitable known intraoperative imaging technology may be used, such as, for example, CT, ultrasound, 2D coordinated fluoroscopy, 3D fluoroscopy, and the like. As an alternative to intraoperative imaging, as is well known, the surface shape of the patient's bone may be mapped using a tracked probe, laser scanner, or other coordinate measuring device that can be inserted into an incision to capture points on the surface of the bone. The captured data is used to generate a cloud of points that can be used to reconstruct the surface of the bone or that can be fused to a bone model or bone atlas as described above.

One result of the implant planning process is that when the surgeon specifies the location of the selected prosthetic device 5 relative to the bone model, the position of the corresponding bone-cutting pattern relative to the bone model is known. This is because the bone-cutting pattern is linked to or associated with the model of the selected prosthetic device 5. In this manner, the appropriate bone-cutting pattern is registered to the model of the bone. As a result, the implant planning process defines the bone cuts that the surgeon needs to make to sculpt the femur 14 to receive the selected prosthetic device 5 in the planned position.

In step S602 (Robotic System Programming), the robotic system 100 is programmed with the implant planning data from step S601, including the model of the bone, the model of the selected prosthetic device 5, the bone-cutting pattern, and the planned implant placement. Alternatively, implant planning may be performed directly on a computing system associated with the robotic system 100 thereby eliminating step S602. Once the robotic system 100 receives the implant planning data, the robotic system 100 knows the location of the bone-cutting pattern relative to the model of the bone.

In step S603 (Registration), the guide structure 200 of the robotic system 100 is registered to the patient using any known registration technique, such as the registration technique described in the above-referenced U.S. Patent Application Pub. No. 2006/0142657. During registration, the location of the patient's bone (i.e., the femur 14) in physical space is correlated to the model of the bone in virtual space. As a result of patient registration, the robotic system 100 knows the location of the patient's physical bone relative to the model of the bone. Thus, based on the implant planning data and the registration data, the robotic system 100 knows the location of the patient's physical bone relative to the bone-cutting pattern.

In step S604 (Bone Preparation), the surgeon manipulates the controllable guide structure 200 of the robotic system 100 to prepare the femur 14 with the cutting tool 220. During cutting, a tracking system in communication with the robotic system 100 tracks the location of the tool 220 and the femur 14 and, in most cases, allows the surgeon to freely move the cutting tool 220 in the surgical workspace. When the tool 220 is in proximity to a cutting boundary of the bone-cutting pattern, however, the control system 300 of the robotic system 100 controls the feedback mechanism to provide force feedback that tends to constrain the surgeon from penetrating the cutting boundary with the tool 220.

After bone sculpting is complete, in step S605 (Trial Reduction and Modification), the surgeon fits a trial implant to the prepared surface of the femur 14 and performs a trial reduction process to assess the fit of the trial implant. During this process, the surgeon can make any desired adjustments or modifications prior to installing the selected prosthetic device 5. Adjustments and modifications may include, for example, repeating implant planning, modifying the bone-cutting pattern, making additional bone cuts, selecting a different prosthetic device 5, and/or the like.

Figure 12B:
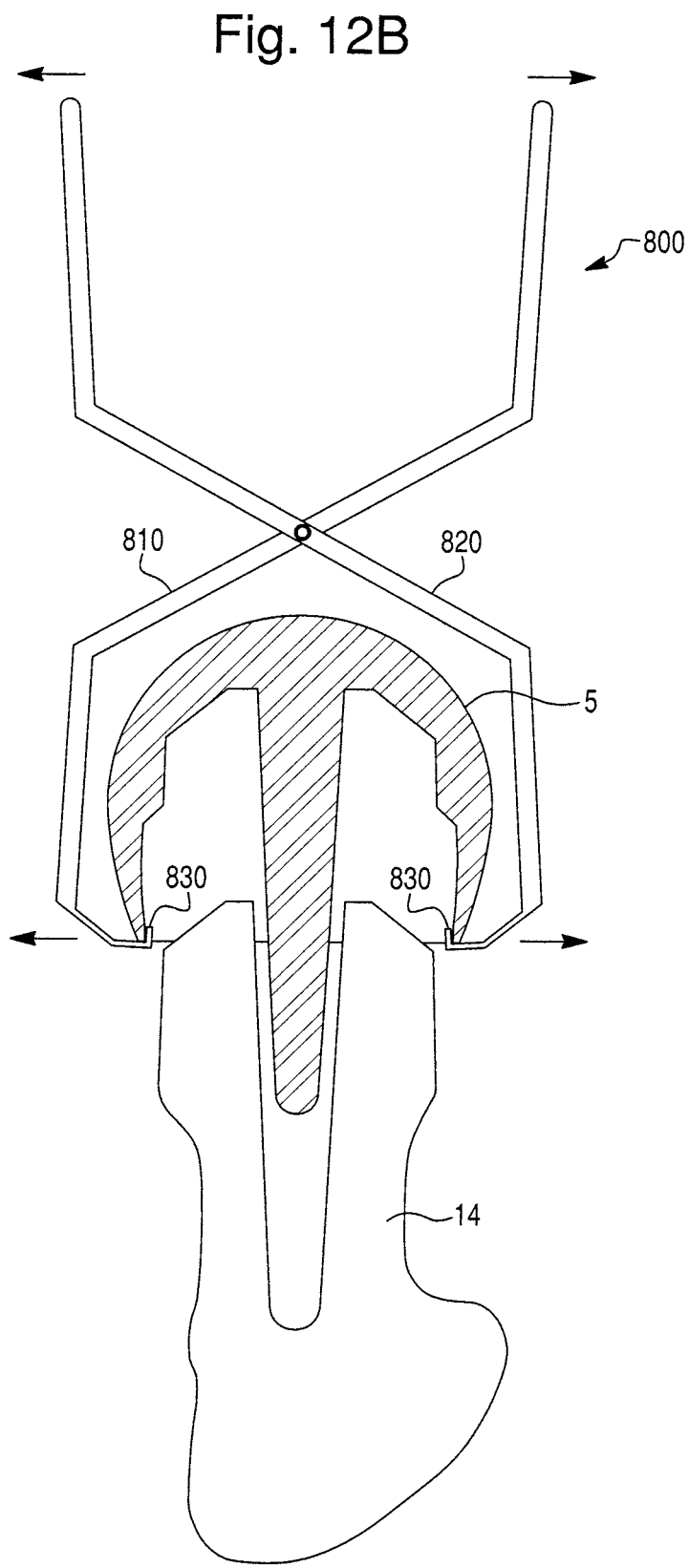
FIG. 12B is an illustration of the installation tool of FIG. 12A in an expanded configuration.
Figure 12C:
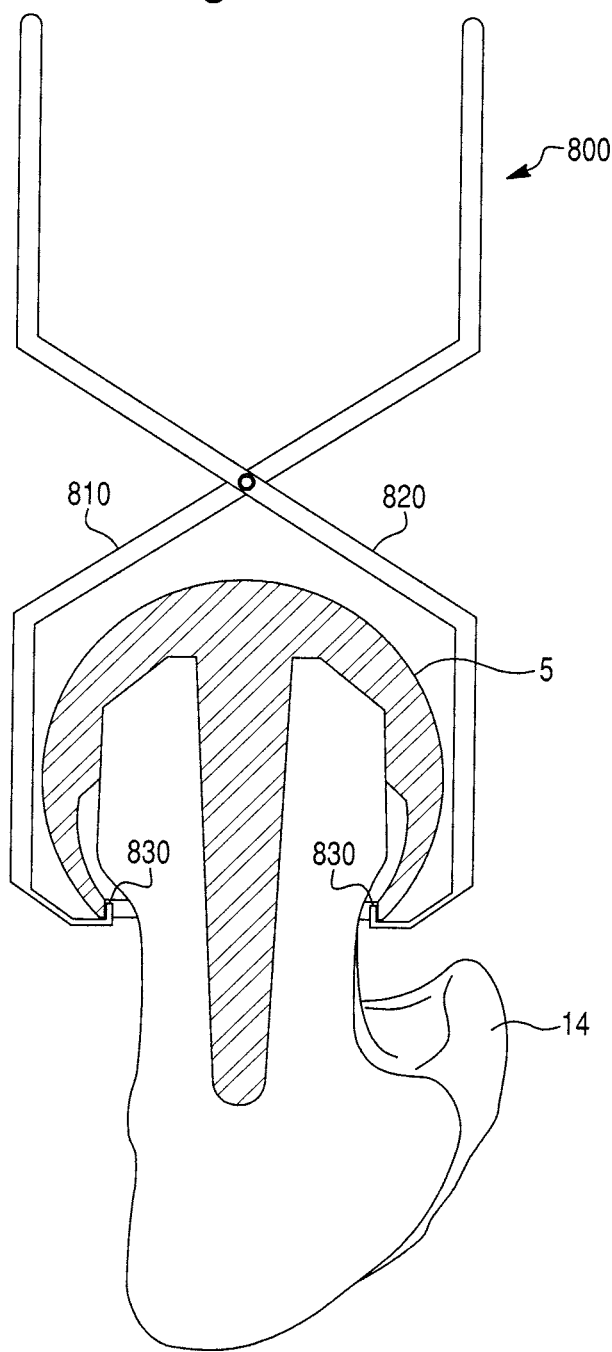
FIG. 12C is an illustration of the installation tool of FIG. 12A in a released configuration.

When the surgeon is satisfied with the preparation of the femur 14 and the performance of the trial implant, in step S606 (Implant Installation), the selected prosthetic device 5 is installed on the femur and fixed in place, for example, via bone cement or a press fit. If the base of the prosthetic device 5 is too narrow to fit completely over the sculpted femoral head 16, the surgeon can use an installation tool 800 to install the prosthetic device 5. In one embodiment, the installation tool 800 is adapted to flare or spread the compliant base of the prosthetic device 5 so that the prosthetic device 5 will fit over the sculpted bone. The installation tool 800 may be any suitable manual or automated device for widening an opening. In one embodiment, shown in FIG. 12A, the installation tool 800 includes a leg 810, a leg 820, and prongs 830 disposed on the distal ends of the legs 810 and 820. The prongs 830 engage the inner surface 60 of the prosthetic device 5 at the distal ends 74 of the extension members 70. As illustrated in FIG. 12B (expanded configuration), when the proximal ends of the legs 810, 820 are actuated to move outward, the distal ends of the legs 810, 820 also move outward causing the extension members 70 that are hooked onto the prongs 830 to flare outward as well. In this manner, the base of the prosthetic device 5 is expanded. The prosthetic device 5 can then be moved onto the femoral head 16. As shown in FIG. 12C (released configuration), once in position, the legs 810, 820 are released, which causes the extension members 70 to at least partially contract. In this manner, the base of the prosthetic device 5 is released. The prongs 830 are then disengaged from the prosthetic device 5 (e.g., by moving the installation tool 800 downward until the prongs 830 clear the distal ends 74 of the prosthetic device 5), and the installation tool 800 is moved into an expanded configuration so that it can be moved over the prosthetic device 5 and out of the joint. In the released configuration, the extension members 70 clamp onto the prepared bone thereby assisting in the fixation of the prosthetic device 5. Although the installation tool 800 shown in FIGS. 12A-12C is configured to engage two extension members 70 that are disposed opposite one another (e.g., 180 degrees apart), other embodiments of the installation tool 800 can be customized based on the design of a particular prosthetic device 5. For example, in other embodiments, the installation tool 800 can be adapted to engage fewer or additional extension members 70 and/or extension members 70 that are disposed at various angular positions on the prosthetic device 5.

Thus, in operation, an embodiment of a surgical method for implanting a prosthetic device in a joint 10 includes preparing a first bone (e.g., the femur 14) of the joint 10 to receive a first component (e.g., the prosthetic device 5); expanding a base of the first component; moving the first component onto the first bone; and releasing the base of the first component to allow the base to at least partially contract. As discussed above, the first bone may optionally include one or more of the raised portions 710, as shown in FIG. 9. If the raised portions 710 are present, the surgical method 600 may further include orienting the first component such that the raised portions 710 of the first bone are aligned with corresponding openings (e.g., the reservoirs 80 and/or the fluid passages 90) on the first component and moving the first component onto the first bone such that the raised portions 710 of the first bone engage the corresponding openings of the first component.

As discussed above, one advantage of the prosthetic device 5 is increased articular contact area, which causes the outer surface 50 of the prosthetic device 5 to remain in contact with a majority of or the entire opposing surface as the joint 10 moves through a range of motion. Accordingly, the surgical method 600 may further include implanting a second component (e.g., the acetabular component 28) on a second bone (e.g., the acetabulum 22) of the joint 10; engaging the first and second components; moving the joint 10 through a range of motion; and maintaining substantial contact between an articular surface of the first component and an articular surface of the second component throughout the range of motion, as shown, for example, in FIG. 7C.

The surgical method described is intended as an exemplary illustration only. In other embodiments, the order of the steps of the method may be rearranged in any manner suitable for a particular surgical application. Additionally, other embodiments may include all, some, or only portions of the steps of the surgical method and may combine the steps of the method with existing and/or later developed surgical approaches.

Thus, according to embodiments of the present invention, an orthopedic joint prosthesis that promotes fluid distribution and reduces the potential for dislocation is provided.

Other embodiments of the invention will be apparent to those skilled in the art from consideration of the specification and practice of the invention disclosed herein. It is intended that the specification and examples be considered as exemplary only.

What is claimed is:

1. A substantially cup-shaped prosthetic device for a joint, comprising:
    an outer surface configured to operatively engage at least one of a first bone of the joint and a component;
    an inner surface including at least a portion configured to connect to a second bone of the joint;
    at least one reservoir having an opening at each of the inner surface and the outer surface and extending therebetween through a wall of the prosthetic device; and
    a plurality of extension members, wherein the reservoir is disposed between adjacent extension members,
    wherein the prosthetic device is a femoral head cup, and
    wherein a distal end of each of the plurality of extension members is located at a base of the femoral head cup.

2. The substantially cup-shaped prosthetic device of claim 1, further comprising at least one fluid passage configured to permit fluid communication between a source of fluid and the reservoir.

3. The substantially cup-shaped prosthetic device of claim 2, wherein the fluid passage is disposed between adjacent extension members.

4. The substantially cup-shaped prosthetic device of claim 3, wherein at least one of the reservoir and the fluid passage comprises an opening between the adjacent extension members.

5. The substantially cup-shaped prosthetic device of claim 3, wherein the distal end of one of the adjacent extension members is separated from the distal end of the other of the adjacent extension members by at least one of the reservoir and the fluid passage.

6. The substantially cup-shaped prosthetic device of claim 3, wherein the distal end of each adjacent extension member includes at least a portion that is configured to flex upon application of a joint force such that the distal end is displaced.

7. The substantially cup-shaped prosthetic device of claim 6, wherein the portion of one of the adjacent extension members is configured to flex at least partially independently of the portion of the other of the adjacent extension members.

8. The substantially cup-shaped prosthetic device of claim 3, wherein an upper portion of the outer surface comprises a hemisphere and the plurality of extension members extend below the hemisphere.

9. The substantially cup-shaped prosthetic device of claim 3, wherein the outer surface of the plurality of extension members has a substantially spherical shape.

10. The substantially cup-shaped prosthetic device of claim 3, wherein each extension member is configured such that the distal end of the extension member does not traverse an edge of the at least one of the first bone and the component as the joint moves through a range of motion.

11. The substantially cup-shaped prosthetic device of claim 3, wherein at least one extension member includes an anti-rotation feature.

12. A substantially cup-shaped prosthetic device for a joint, comprising:
    an outer surface configured to operatively engage at least one of a first bone of the joint and a component;
    an inner surface including a portion configured to connect to a second bone of the joint;
    a first deflection member including a distal end and at least a portion that is configured to flex upon application of a force such that the distal end is displaced; and
    a second deflection member including a distal end and at least a portion that is configured to flex upon application of a force such that the distal end is displaced,
    wherein the first and second deflection members are separated by at least one opening in a wall of the prosthetic device such that the portion of the first deflection member is configured to flex at least partially independently of the portion of the second deflection member,
    wherein the prosthetic device is a femoral head cup, and
    wherein the distal ends of the first and second deflection members are located at a base of the femoral head cup.

13. The substantially cup-shaped prosthetic device of claim 12, wherein at least one of the first and second deflection members includes an anti-rotation feature.

14. The substantially cup-shaped prosthetic device of claim 12, wherein an upper portion of the outer surface comprises a hemisphere and the first and second deflection members extend below the hemisphere.

15. The substantially cup-shaped prosthetic device of claim 12, wherein the first and second deflection members extend a substantially spherical shape of the outer surface.

16. The substantially cup-shaped prosthetic device of claim 12, wherein the first and second deflection members taper in width toward free ends thereof.

17. The substantially cup-shaped prosthetic device of claim 12, wherein the first and second deflection members taper in thickness toward free ends thereof.

18. The substantially cup-shaped prosthetic device of claim 12, further comprising a third deflection member, and wherein the first, second, and third deflection members are uniformly sized and evenly spaced apart from one another by openings in the wall.

19. The substantially cup-shaped prosthetic device of claim 12, wherein the at least one opening has a perimeter edge that is rounded at the outer surface.

20. A substantially cup-shaped femoral head cup for a joint, comprising:
    an outer surface configured to operatively engage at least one of a first bone of the joint and a component;
    an inner surface including at least a portion configured to connect to a second bone of the joint;
    a plurality of reservoirs having an opening at each of the inner surface and the outer surface and extending therebetween through a wall of the femoral head cup; and
    a plurality of fluid passages, each extending from a base of the femoral head cup to one of the plurality of reservoirs such that the fluid passages are open at the base and a plurality of extension members are formed,
    wherein a distal end of each of the plurality of extension members is located at the base of the femoral head cup.

* * * * *